(12) United States Patent
Güner et al.

(10) Patent No.: US 11,236,053 B2
(45) Date of Patent: Feb. 1, 2022

(54) NADPH OXIDASE INHIBITORS AND USES THEREOF

(71) Applicants: Emory University, Atlanta, GA (US); Mercer University, Atlanta, GA (US); Howard University, Washington, DC (US); Union University, Jackson, TN (US)

(72) Inventors: Osman Güner, Rohnert Park, CA (US); Bernard Lassegue, Decatur, GA (US); Kathy Griendling, Stone Mountain, GA (US); Qian Xu, Changsha (CN); David Brown, Durham, NC (US); J. Phillip Bowen, Atlanta, GA (US); Amol Kulkarni, Silver Spring, MD (US); E. Blake Watkins, Jackson, TN (US)

(73) Assignees: Emory University, Atlanta, GA (US); Mercer University, Atlanta, GA (US); Howard University, Washington, DC (US); Union University, Jackson, TN (US)

( * ) Notice: Subject to any disclaimer, the term of this patent is extended or adjusted under 35 U.S.C. 154(b) by 0 days.

(21) Appl. No.: 16/634,567

(22) PCT Filed: Jul. 26, 2018

(86) PCT No.: PCT/US2018/043890
§ 371 (c)(1),
(2) Date: Jan. 27, 2020

(87) PCT Pub. No.: WO2019/023448
PCT Pub. Date: Jan. 31, 2019

(65) Prior Publication Data
US 2020/0270214 A1 Aug. 27, 2020

Related U.S. Application Data

(60) Provisional application No. 62/537,267, filed on Jul. 26, 2017.

(51) Int. Cl.
| | |
|---|---|
| C07D 239/26 | (2006.01) |
| C07D 213/50 | (2006.01) |
| C07D 307/54 | (2006.01) |
| C07D 215/14 | (2006.01) |
| C07D 213/65 | (2006.01) |

(52) U.S. Cl.
CPC ......... *C07D 239/26* (2013.01); *C07D 213/50* (2013.01); *C07D 213/65* (2013.01); *C07D 215/14* (2013.01); *C07D 307/54* (2013.01)

(58) Field of Classification Search
CPC .................................................. C07D 239/26
See application file for complete search history.

(56) References Cited

U.S. PATENT DOCUMENTS

| | | | |
|---|---|---|---|
| 4,276,290 | A | 6/1981 | Weir |
| 5,691,335 | A | 11/1997 | Fukami |
| 7,625,902 | B2 | 12/2009 | Dehmlow |
| 8,389,518 | B2 | 3/2013 | Page |
| 2014/0194422 | A1 | 7/2014 | Ganesh |

FOREIGN PATENT DOCUMENTS

WO 2017046739 3/2017

OTHER PUBLICATIONS

Tkaczynski et al (1996): STN International CAPLUS database, (Columbus, Ohio), Accession No. 1996: 641400.*
Babczinski et al. Substituted Tetrahydropyrimidinones: A New Herbicidal Class of Compounds Inducing Chlorosis by Inhibition of Phytoene Desaturation, Pesticide Biochemistry and Physiology 52, 45-59 (1995).
Borbely et al. Small-Molecule Inhibitors of NADPH Oxidase 4, J. Med. Chem. 2010, 53, 6758-6762.
Brown et al. Identification and characterization of a novel Nox4 inhibitor, Emory University poster, 2013.
Casas et al. NOX4-dependent neuronal autotoxicity and BBB breakdown explain the superior sensitivity of the brain to ischemic damage, PNSA, 2017, 114, 46, 12315-12320.
El-Deeb et al. Synthesis and antitumor evaluation of novel cyclic arylsulfonylureas: ADME-T and pharmacophore prediction, European Journal of Medicinal Chemistry 45 (2010) 2516e2530.
Laleu et al. First in Class, Potent, and Orally Bioavailable NADPH Oxidase Isoform 4 (Nox4) Inhibitors for the Treatment of Idiopathic Pulmonary Fibrosis, J. Med. Chem. 2010, 53, 7715-7730.
Lassegue et al. NADPH Oxidases: Functions and Pathologies in the Vasculature, Arterioscler Thromb Vasc Biol. 2010;30:653-661.
Ma et al. NADPH oxidase in brain injury and neurodegenerative disorders, Molecular Neurodegeneration (2017) 12:7, 1-28.
Martin-Garrido et al. NADPH Oxidase 4 Mediates TGF-β-Induced Smooth Muscle α-Actin Via p38MAPK and SRF, Free Radic Biol Med. 2011, 50(2): 354-362.
Morre et al. Antitumor sulfonylurea-inhibited NADH oxidase of cultured HeLa cells shed into media, Biochimica et Biophysica Acta 1280 (1996) 197-206.
Morre et al. The Sulfonylurea-Inhibited NADH Oxidase Activity of HeLa Cell Plasma Membranes has Properties of a Protein Disulfide-Thiol Oxidoreductase with Protein Disulfide-Thiol Interchange Activity, Journal of Bioenergetics and Biomembranes, vol. 30, No. 5, 1998.

(Continued)

*Primary Examiner* — Golam M Shameem
(74) *Attorney, Agent, or Firm* — Emory Patent Group

(57) ABSTRACT

This disclosure relates to compounds and methods of treating or preventing a Nox related disease or condition comprising administering to a subject in need thereof a Nox inhibitor or pharmaceutical compositions comprising a Nox inhibitor disclosed herein, derivatives, or compounds disclosed herein optionally substituted with one or more substitutes including optional salt and prodrug forms. In certain embodiments, this disclosure relates to sulfonylurea compounds and uses reported herein.

19 Claims, 6 Drawing Sheets

(56) References Cited

OTHER PUBLICATIONS

Przybylska et al. NOX4 downregulation leads to senescence of human vascular smooth muscle cells, Oncotarget, vol. 7, No. 41, 2016.
Pubchem, CID 15211183, 1-(4-Methylphenyl)sulfonyl-3-phenylimidazolidin-2-one, available at https://pubchem.ncbi.nlm.nih.gov/compound/15211183, downloaded Feb. 24, 2021.
Watkins et al. Discovery and Therapeutic Relevance of Small-Molecule NOX4 Inhibitors, Chapter 8, 2018 Medicinal Chemistry Reviews, Medicinal Chemistry Division of the American Chemical Society.
Xu et al. Design, synthesis, and biological evaluation of inhibitors of the NADPH oxidase, Nox4, Bioorg Med Chem, 2018, 26(5):989-998.

* cited by examiner 23 n=1, R = OCH$_3$
24 n=0, R = F
25 n=0, R = OCH$_3$

NADPH OXIDASE INHIBITORS AND USES THEREOF

CROSS-REFERENCE TO RELATED APPLICATIONS

This application is the National Stage of International Application No. PCT/US2018/043890 filed Jul. 26, 2018, which claims the benefit of U.S. Provisional Application No. 62/537,267 filed Jul. 26, 2017. The entirety of each of these applications is hereby incorporated by reference for all purposes.

STATEMENT REGARDING FEDERALLY SPONSORED RESEARCH OR DEVELOPMENT

This invention was made with government support under HL095070 awarded by the National Institutes of Health. The government has certain rights in the invention.

BACKGROUND

NADPH oxidases (Nox enzymes) are mediators of both physiologic and pathophysiologic processes. Nox enzymes catalyze NADPH-dependent generation of reactive oxygen species (ROS), including superoxide and hydrogen peroxide. Nox4 plays a role in fibrosis, as well as a host of pathologies and diseases. Borbély et al. report small-molecule inhibitors of NADPH Oxidase 4. J. Med. Chem., 2010, 53 (18), 6758-6762.

Traumatic brain injury and neurodegenerative disorders such as Alzheimer's disease and Parkinson's disease are major public health issues as they lack satisfactory treatment options. Thus, there is a need to identify improved therapeutic methods. Ma et al. report that genetic and pharmacological inhibition of NADPH oxidase (Nox) enzymes are neuroprotective and able to reduce detrimental aspects of pathology following ischemic and traumatic brain injury, as well as in chronic neurodegenerative disorders. Mol Neurodegener, 2017, 12(1):7. Casas et al. report cell death was significantly reduced in hippocampal brain slices treated with Nox 4 inhibitors: GKT136901 and VAS2870. Proc Natl Acad Sci USA, 2017, 114(46): 12315-12320. See also Page et al. Pyrazolo pyridine derivatives as NADPH oxidase inhibitors, U.S. Pat. No. 8,389,518 (2013).

References cited herein are not an admission of prior art.

SUMMARY

It has been discovered that certain compounds inhibit Nox enzymes and/or reduce $H_2O_2$ production. In certain embodiments, this disclosure relates to compounds and methods of treating or preventing a Nox related disease or condition comprising administering to a subject in need thereof an effective amount of a Nox inhibitor or pharmaceutical compositions comprising a Nox inhibitor disclosed herein, or compounds disclosed herein optionally substituted with one or more substitutes including optional salt and prodrug forms.

In certain embodiments, this disclosure relates to compounds having formula I.

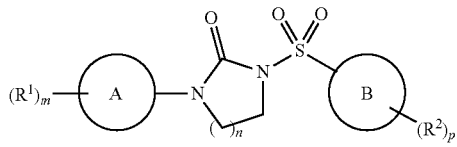

Formula I derivatives, prodrugs, esters, or salts thereof wherein,
ring A is a carbocyclyl, aryl, or heterocyclyl;
ring B is a carbocyclyl, aryl, or heterocyclyl;
n is 1 or 2;
m is 1, 2, 3, or 4;
p is 1, 2, 3, or 4;
$R^1$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{15}$;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;
$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;
$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to a pharmaceutical comprising a compound as described herein including salts and prodrugs thereof and a pharmaceutically acceptable excipient, diluent, or carrier. In certain embodiments, the pharmaceutical composition is in the form of a tablet, pill, capsule, gel, or aqueous buffered solution.

In certain embodiments, the disclosure relates to uses of compounds disclosed herein in the production of a medicament for the treatment of Nox related conditions.

In certain embodiments, the disclosure relates to pharmaceutical compositions comprising a compound as described herein and another active ingredient.

In certain embodiments, the disclosure relates to administering compositions disclosed herein in combination with another active agent in the treatment of a Nox related condition.

In certain embodiments, the disclosure relates to uses of a compound as described herein for the treatment of kidney and lung fibrosis, cancer, stroke, cardiac hypertrophy, cardiac contractile dysfunction, diabetic nephropathy, arthritis, osteoporosis, peripheral nerve injury, atherosclerosis, aneurysms and pulmonary hypertension.

In certain embodiments, the disclosure relates to methods of treating or preventing cancer comprising administering pharmaceutical composition comprising a compound as described herein optionally in combination with another active ingredient to a subject in need thereof. In further embodiments, the subject is at risk of, exhibiting symptoms of, or diagnosed with cancer.

In certain embodiments, the Nox related disease or condition is a neurological disorder. In certain embodiments, the neurological disorder Alzheimer's disease, Parkinson's disease, Huntington's disease, amyotrophic lateral sclerosis, or multiple sclerosis.

In certain embodiments, the Nox related disease or condition is ischemic injury, ischemia-reperfusion (IR) injury, traumatic brain injury, myocardial infarction (MI), peripheral artery disease, or stroke.

In certain embodiments, the Nox related disease or condition is a cardiovascular disorder, respiratory disorder, metabolism disorder, skin disorder, bone disorder, neuroinflammatory and/or neurodegenerative disorder, kidney disease, reproduction disorder, diseases affecting the eye and/or the lens and/or conditions affecting the inner ear, inflammatory disorder, liver disease, pain, cancer, allergic disorder, traumatisms, septic, hemorrhagic and anaphylactic shock, diseases or disorder of the gastrointestinal system, and angiogenesis.

In certain embodiments, the disclosure relates to methods of making compounds disclosed herein comprising mixing starting materials and reagents under conditions such that the product is formed.

In certain embodiments, the disclosure relates to methods of analyzing inhibitory properties against Nox enzymes. In certain embodiments, the disclosure relates to methods of analyzing novel compounds against Nox4.

In certain embodiments, compounds disclosed herein can be for use as a medicament. In certain embodiments, compounds disclosed herein can be use in the treatment of a Nox related disease or condition. In certain embodiments, use of a compound disclosed herein are for the manufacture of a medicament for treatment of a Nox related disease or condition.

DETAILED DESCRIPTION

Figure 1:
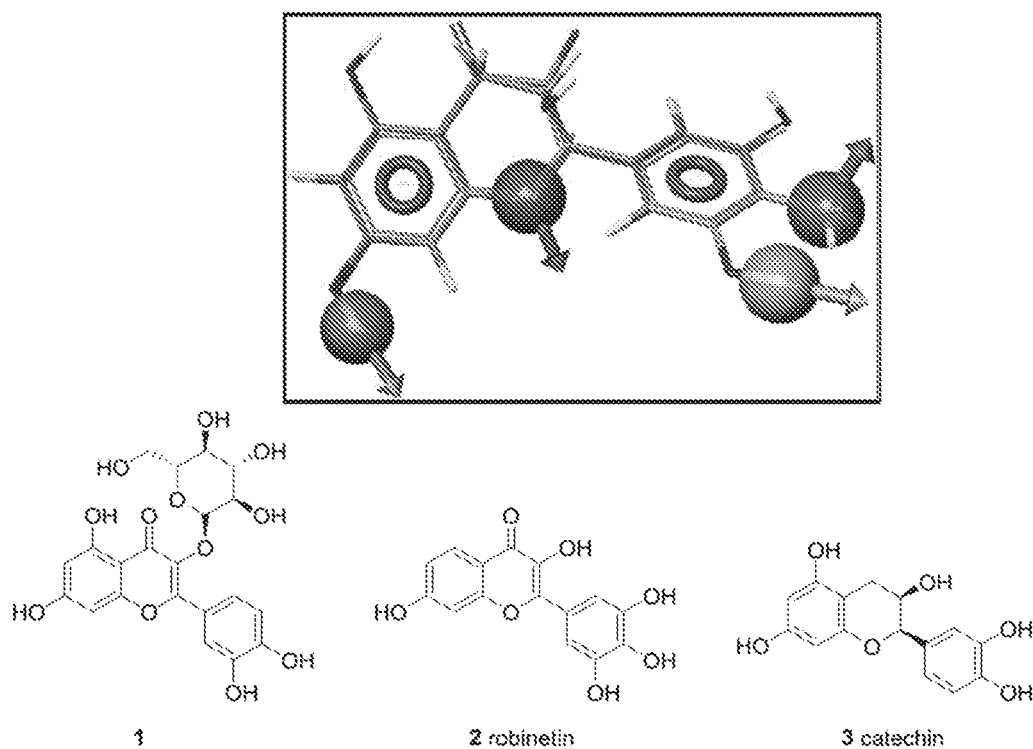
FIG. 1 illustrates two antioxidants retrieved by the pharmacophore model (top) based on (1): robinetin (2) and catechin (3). The six-feature pharmacophore model included two hydrogen-bond acceptors, two hydrogen-bond donors and two aromatic rings.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

To the extent that structures provided herein are compounds with tautomers by hydrogen migration, a skilled artisan would understand the formula to cover all tautomeric forms.

As used herein, "alkyl" means a noncyclic straight chain or branched, unsaturated or saturated hydrocarbon such as those containing from 1 to 10 carbon atoms, typically 1 to 4 otherwise designated $C_{1-4}$alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Aminoalkyl" refers to an amino group attached through an alkyl bridge as defined above (i.e., NH$_2$-alkyl-).

"Alkanoyl" refers to an alkyl as defined above attached through a carbonyl bridge (i.e., —(C═O)alkyl).

"Alkylsulfonyl" refers to an alkyl as defined above attached through a sulfonyl bridge (i.e., —S(═O)$_2$alkyl) such as mesyl and the like, and "arylsulfonyl" refers to an aryl attached through a sulfonyl bridge (i.e., —S(═O)$_2$aryl).

"Alkylsulfamoyl" refers to an alkyl as defined above attached through a sulfamoyl bridge (i.e., —NHS(═O)$_2$alkyl), and an "Arylsulfamoyl" refers to an alkyl attached through a sulfamoyl bridge (i.e., —NHS(═O)$_2$aryl).

"Alkylsulfinyl" refers to an alkyl as defined above attached through a sulfinyl bridge (i.e. —S(═O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(═O)R$_b$, —NR$_a$C(═O)NR$_a$NR$_b$, —NR$_a$C(═O)OR$_b$, —NR$_a$SO$_2$R$_b$, —C(═O)R$_a$, —C(═O)OR$_a$, —C(═O)NR$_a$R$_b$, —OC(═O)NR$_a$R$_b$, —OR$_a$, —SR$_a$, —SOR$_a$, —S(═O)$_2$R$_a$, —OS(═O)$_2$R$_a$ and —S(═O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "allergic disorder" includes hay fever and asthma.

The term "disease or disorder affecting the metabolism" includes obesity, metabolic syndrome, and associated fatty liver (steatosis), Non-alcoholic fatty liver disease (NAFLD), nonalcoholic steatohepatitis, and Type II diabetes.

The term "skin disease" or disorder" includes psoriasis, eczema, dermatitis, wound healing and scar formation.

The term "bone disorder" includes osteoporosis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuro-inflammatory and demyelinating states or diseases such as leukoencephalopathies, and leukodystrophies.

The term "demyelinating" is referring to a state or a disease of the CNS comprising the degradation of the myelin around the axons. In the context of the disclosure, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the disclosure includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbycusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound disclosed herein in a sufficient dose to inhibit NADPH oxidase.

The term liver diseases or disorders include liver fibrosis, alcohol induced fibrosis, steatosis and non-alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound disclosed herein in a sufficient dose to inhibit NADPH oxidase.

The term "pain" includes hyperalgesia associated with inflammatory pain.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

Contemplated cancer include, but are not limited to, carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer) or the related diseases which require the administration to a mammal in a therapeutic effective dose of a compound disclosed herein in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "pharmacophore model" refers a description of the conformation of a compound within the appropriate target binding site through molecular features, e.g., an ensemble of steric and electronic features, which are necessary for molecular recognition of a ligand by a biological macromolecule. Typical pharmacophore features include hydrophobic centroids, aromatic rings, hydrogen bond acceptors or donors, cations, and anions. These pharmacophoric points may be located on the ligand itself or may be projected points presumed to be located in the receptor. Pharmacophore models are used to define features of one or more atom, e.g., hydrophobic volumes and hydrogen bond vectors. A database of diverse chemical compounds can then be searched for more molecules which share the same features arranged in the same relative orientation.

A pharmacophore model defines the three-dimensional (3D) arrangement of the features of a molecule that are assumed important for the molecule's biological activity. Such arrangements are required in order for the compound to enter, transport, and bind to the receptor active site. The features are abstract definitions such as hydrogen-bond acceptors, or donors, lipophilic groups, and positive or negative ionizable groups.

Figure 9:
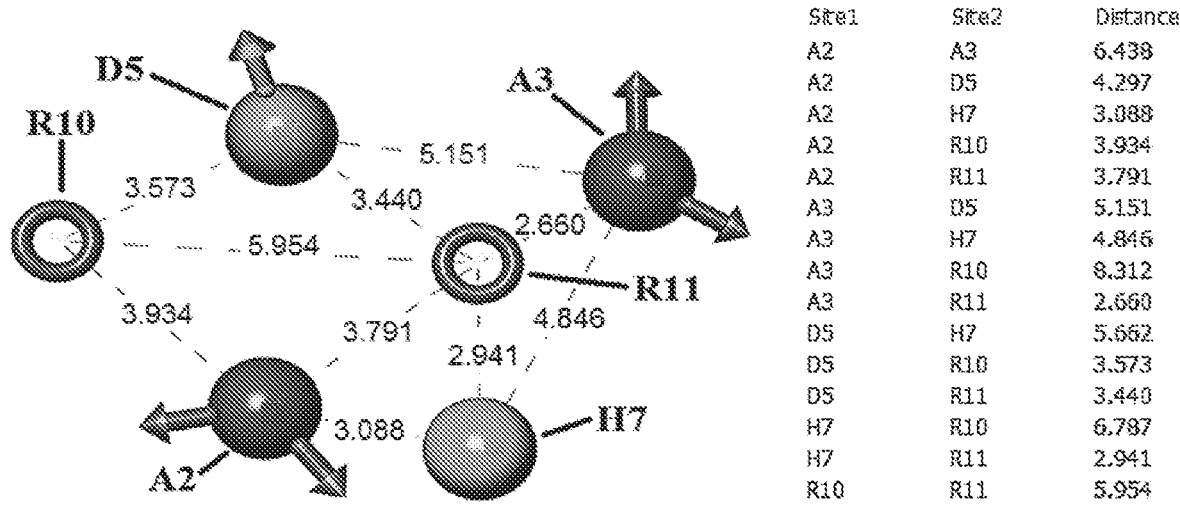
FIG. 9 shows the representative pharmacophore model wherein the functions of A2 hydrogen bond acceptor, A3 hydrogen bond acceptor, D5 hydrogen bond donor, H7 hydrophobic volume, R10 hydrophobic centroid, and R11 hydrophobic centroid are illustrated. The table provides distances between pharmacophore centers and corresponding distances between the centers of each site.

The pharmacophore models are described with the distances and angles between such features and compounds can fit onto these models within a given tolerance. For example, if the model defines that a H-bond donor and a positive ionizable group should be 5 Å apart from each other, the compound is assumed to fit onto the model if it attains a conformation that contains such two groups that are 5±1 Å apart from each other. The angles between three such features are deemed fitting if they can attain the defined angle within ±5 degrees. Typically, there will be 5 to 6 such features with geometrical requirements and they need to be satisfied simultaneously, or 5 out of 6 features should satisfy, etc. if the model is defined in such terms. In certain embodiments, the compound or as defined in a formula disclosed herein fits onto a pharmacophore model criteria with ±1 Å tolerance as provided in FIG. 9.

NADPH Oxidase

The NADPH oxidase family of enzymes plays a role in a variety of physiological and pathophysiological responses. It consists of one single subunit (Nox5) and six multi-subunit enzymes (Nox1, Nox2, Nox3, Nox4, Duox1, and Duox2). Of particular interest, Nox4 is widely distributed in a variety of tissues including kidney, lung, liver, as well as heart and vasculature. Nox4 influences multiple biological functions by constitutively generating $H_2O_2$. Thus, small-molecule pharmacologic inhibitors of Nox4 may be used to address a wide spectrum of diseases.

Recent work using cultured cells and genetically modified animals has shed new light on the biological functions of Nox4. Nox4 favors vasodilation and thus lowers blood pressure, enhances capillary angiogenesis in ischemic limbs, and inhibits angiotensin II-induced vascular inflammation and remodeling. On the other hand, a plethora of studies suggest that Nox4 also contributes to disease development, especially in situations involving ischemia or fibrosis. In fact, an increasing number of human studies indicate that biosynthesis of Nox4 is upregulated in various diseases including hypertension, cardiac hypertrophy, atherosclerosis, diabetic nephropathy, pulmonary hypertension, and pulmonary fibrosis.

In streptozotocin-induced diabetic rats, expression of Nox4 is increased and deletion of Nox4 is reno-protective. Nox4 also contributes to the atherosclerotic phenotype in smooth muscle and potentially mediates cardiac hypertrophy in response to phenylephrine and pressure overload. Compared to wild-type mice, global Nox4 knockout animals showed attenuated liver injury, inflammation, and fibrosis after injury. Cardiac-specific Nox4 knockout mice have less apoptosis, hypertrophy, interstitial fibrosis, and better cardiac function. Nox4 has been shown to have important roles in pulmonary fibrosis as well. In addition, Nox4 in the hypothalamic paraventricular nucleus contributes to hypertension induced by aldosterone and salt in mice, and a small isoform of Nox4 mediates TLR4-induced apoptosis during renal ischemia/reperfusion injury. Other important pathophysiological roles of Nox4 include promoting the loss of bone mass in osteoporosis, contributing to lung vascular permeability induced by *Pseudomonas aeruginosa*, promoting glomerular lesions in a mouse model of diabetic nephropathy, and mediating fibrosis formation in response to TGF-β. Moreover, Nox4 plays an important role in abnormal neuropharmacology by contributing to hypoxia-promoted tumor progression in glioblastoma multiforme, as well as increasing the severity of brain lesions in a model of ischemic stroke.

Compounds and Derivatives

In certain embodiments, the disclosure relates to compounds disclosed herein, derivatives, prodrugs, esters, or salts and compositions thereof. Although it is not intended that certain embodiments of the disclosure be limited by any particular mechanism it is believed that these compounds are Nox4 modulators.

In certain embodiments, compounds include those having formula I

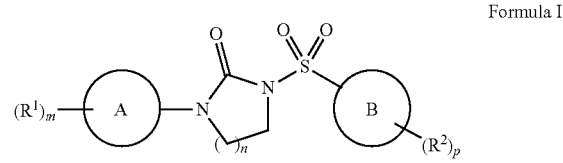

Formula I derivatives, prodrugs, esters, or salts thereof wherein,
ring A is a carbocyclyl, aryl, or heterocyclyl;
ring B is a carbocyclyl, aryl, or heterocyclyl;
n is 1 or 2;
m is 1, 2, 3, or 4;
p is 1, 2, 3, or 4;

$R^1$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{15}$;

$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;

$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;

$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds include those having formula IA:

Formula IA

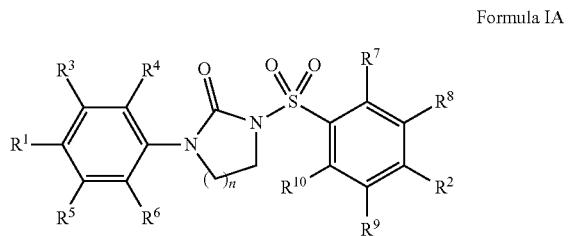

derivatives, prodrugs, esters, or salts thereof wherein,
n is 1 or 2;

$R^1$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^3$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^4$ is hydrogen halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^5$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^6$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^7$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^8$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^9$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl; and $R^{10}$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl.

In certain embodiments, compounds include those having formula IB:

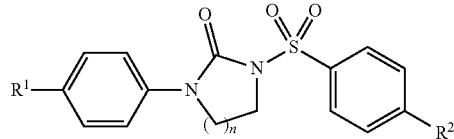

Formula IB derivatives, prodrugs, esters, or salts thereof wherein,
n is 1 or 2;
$R^1$ is alkyl optionally substituted with one or more substituents; and
$R^2$ is halogen or alkoxy optionally substituted with one or more substituents.

In certain embodiments, $R^1$ is alkyl substituted with one or halogen.

In certain embodiments, $R^1$ is trifluoromethyl.

In certain embodiments, $R^2$ is halogen or alkoxy.

In certain embodiments, the Nox inhibitor is selected from: 1-((4-methoxyphenyl)sulfonyl)-3-(4-(trifluoromethyl)phenyl)tetrahydropyrimidin-2(1H)-one; 1-((4-fluorophenyl)sulfonyl)-3-(4-(trifluoromethyl)phenyl)tetrahydropyrimidin-2(1H)-one; and 1-((4-methoxyphenyl)sulfonyl)-3-(4-(trifluoromethyl)phenyl)imidazolidin-2-one.

In certain embodiments, contemplated compounds include those comprising Formula II,

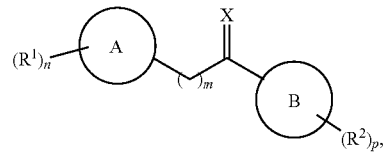

Formula II derivatives, prodrugs, esters, or salts thereof wherein,
ring A is a carbocyclyl, aryl, or heterocyclyl;
ring B is a carbocyclyl, aryl, or heterocyclyl;
m is 1 or 2;
X is O, S, $CH_2$, NH;
n is 1, 2, 3, or 4;
p is 1, 2, 3, 4 or 5;
$R^1$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{15}$;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;
$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;
$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is hydrogen, alkyl or alkoxy, wherein $R^1$ is optionally substituted with one or more, the same or different, $R^{15}$.

In certain embodiments, $R^2$ is hydrogen, alkyl or alkoxy, wherein $R^2$ is optionally substituted with one or more, the same or different, $R^{15}$.

In certain embodiments, formula II is formula IIA,

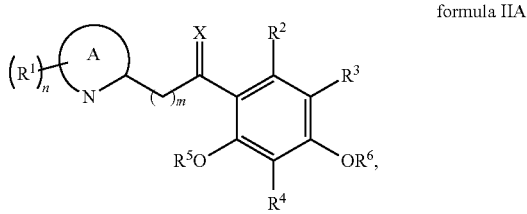

formula IIA derivatives, prodrugs, esters, or salts thereof wherein,
ring A is a heterocyclyl;
m is 1 or 2;
n is 1, 2, 3, or 4;
X is O, S, $CH_2$, NH;
$R^1$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{15}$;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^3$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{15}$;
$R^4$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{15}$;
$R^5$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{15}$;
$R^6$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{15}$;
$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;
$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;
$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-ethyl-N-ethylsulfamoyl, carbocyclyl, aryl, or heterocyclyl.

In certain embodiments, $R^1$ is hydrogen, alkyl or alkoxy, wherein $R^1$ is optionally substituted with one or more, the same or different, $R^{15}$.

In certain embodiments, $R^2$ is hydrogen, alkyl or alkoxy, wherein $R^2$ is optionally substituted with one or more, the same or different, $R^{15}$.

In certain embodiments, $R^3$ is hydrogen, alkyl or alkoxy, wherein $R^3$ is optionally substituted with one or more, the same or different, $R^{15}$.

In certain embodiments, $R^4$ is hydrogen, alkyl or alkoxy, wherein $R^4$ is optionally substituted with one or more, the same or different, $R^{15}$.

In certain embodiments, $R^5$ is hydrogen or alkyl, wherein $R^5$ is optionally substituted with one or more, the same or different, $R^{15}$.

In certain embodiments, $R^6$ is hydrogen or alkyl, wherein $R^6$ is optionally substituted with one or more, the same or different, $R^{15}$.

In certain embodiments, formula II is formula IIB,

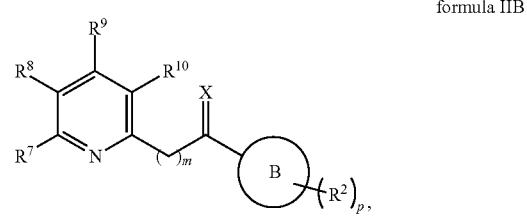

formula IIB derivatives, prodrugs, esters, or salts thereof wherein,
ring B is a carbocyclyl, aryl, or heterocyclyl;
m is 1 or 2;
p is 1, 2, 3, 4, or 5;
X is O, S, $CH_2$, NH;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^7$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{15}$;
$R^8$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{15}$;

$R^9$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{15}$;

$R^{10}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{15}$;

$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;

$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is hydrogen, alkyl or alkoxy, wherein $R^2$ is optionally substituted with one or more, the same or different, $R^{15}$.

In certain embodiments, $R^7$ is hydrogen, alkyl or alkoxy, wherein $R^7$ is optionally substituted with one or more, the same or different, $R^{15}$.

In certain embodiments, $R^8$ is hydrogen, alkyl or alkoxy, wherein $R^8$ is optionally substituted with one or more, the same or different, $R^{15}$.

In certain embodiments, $R^9$ is hydrogen or alkyl, wherein $R^9$ is optionally substituted with one or more, the same or different, $R^{15}$.

In certain embodiments, $R^{10}$ is hydrogen or alkyl, wherein $R^{10}$ is optionally substituted with one or more, the same or different, $R^{15}$.

In certain embodiments, formula II is formula III,

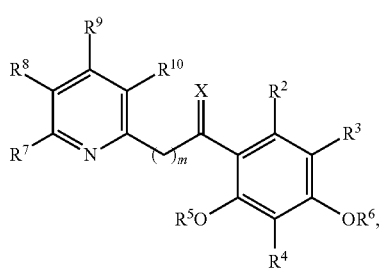

formula III derivatives, prodrugs, esters, or salts thereof wherein, m is 1 or 2;

X is O, S, CH$_2$, NH;

$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;

$R^3$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{15}$;

$R^4$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{15}$;

$R^5$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{15}$;

$R^6$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{15}$;

$R^7$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{15}$;

$R^8$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{15}$;

$R^9$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{15}$;

$R^{10}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{15}$;

$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;

$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, formula II is formula IV, V, or VI, formula IV

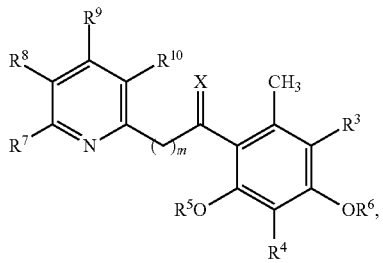

formula V

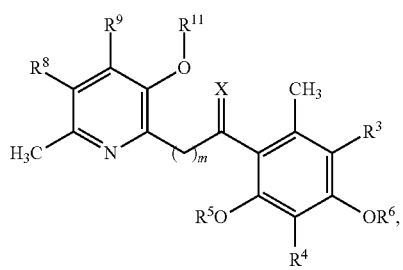

formula VI

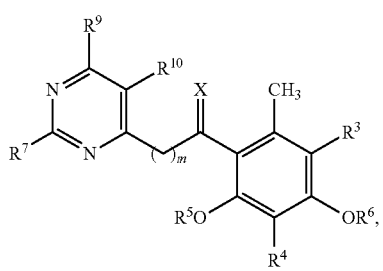

derivatives, prodrugs, esters, or salts thereof wherein,
m is 1 or 2;
X is O, S, $CH_2$, NH;
$R^3$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{15}$;

$R^4$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{15}$;

$R^5$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{15}$;

$R^6$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{15}$;

$R^7$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{15}$;

$R^9$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{15}$;

$R^{10}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{15}$;

$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;

$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, formula II is formula IIC or IID,

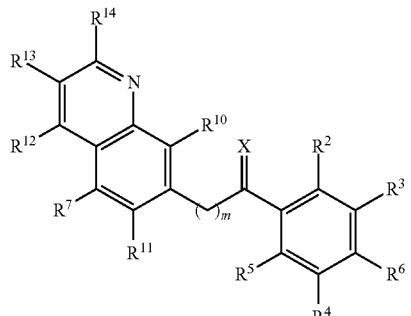

formula IIC

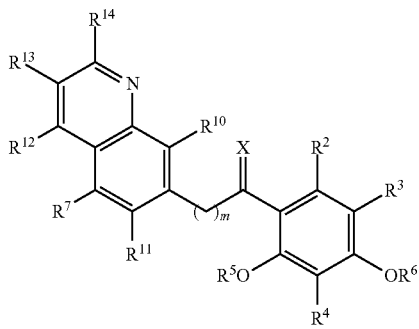

formula IID derivatives, prodrugs, esters, or salts thereof wherein,
m is 1 or 2;
X is O, S, $CH_2$, NH;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^3$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{15}$;
$R^4$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{15}$;
$R^5$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{15}$;
$R^6$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{15}$;
$R^7$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{15}$;
$R^{10}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{15}$;
$R^{11}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{15}$;
$R^{12}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{15}$;
$R^{13}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{15}$;
$R^{14}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$;
$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;
$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;
$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, formula II is formula IIE or IIF,

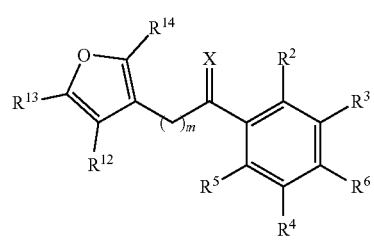

formula IIE

-continued formula IIF

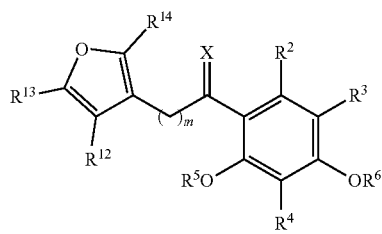

derivatives, prodrugs, esters, or salts thereof wherein,
m is 1 or 2;
X is O, S, CH$_2$, NH;
R$^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^2$ is optionally substituted with one or more, the same or different, R$^{15}$;
R$^3$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^{15}$;
R$^4$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^4$ is optionally substituted with one or more, the same or different, R$^{15}$;
R$^5$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^5$ is optionally substituted with one or more, the same or different, R$^{15}$;
R$^6$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^6$ is optionally substituted with one or more, the same or different, R$^{15}$;
R$^{12}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{15}$;
R$^{13}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{13}$ is optionally substituted with one or more, the same or different, R$^{15}$;
R$^{14}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{14}$ is optionally substituted with one or more, the same or different, R$^{15}$;
R$^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{15}$ is optionally substituted with one or more, the same or different, R$^{16}$;
R$^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{16}$ is optionally substituted with one or more, the same or different, R$^{17}$;
R$^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of formula II are the following compounds or derivatives thereof.

formula XIII

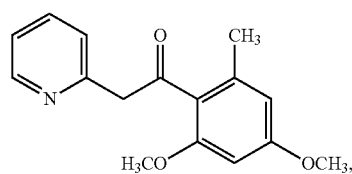

formula XIV

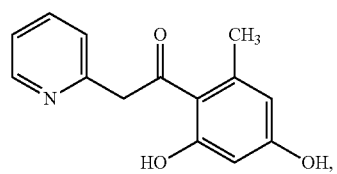

formula XV

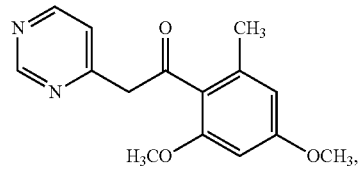

formula XVI

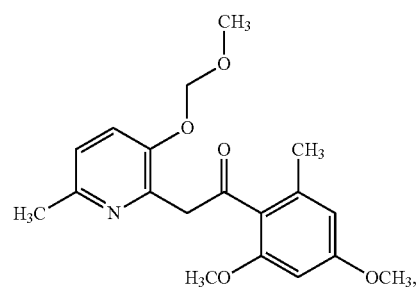

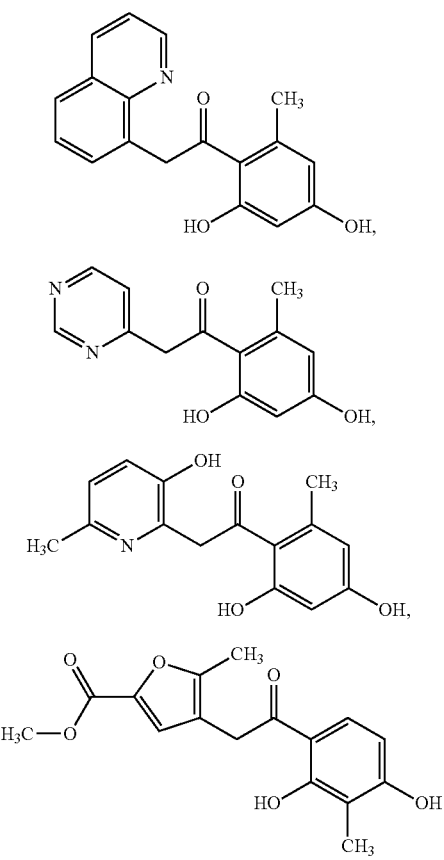

derivatives, prodrugs, esters, or salts thereof.

Methods of Use

The NADPH oxidase family of enzymes plays a role in a variety of physiological and pathophysiological responses. It consists of one single subunit (Nox5) and six multi-subunit enzymes (Nox1, Nox2, Nox3, Nox4, Duox1, and Duox2). Of particular interest, Nox4 is widely distributed in a variety of tissues including kidney, lung, liver, as well as heart and vasculature. Nox4 influences multiple biological functions by constitutively generating $H_2O_2$. Nox4 favors vasodilation and thus lowers blood pressure, enhances capillary angiogenesis in ischemic limbs, and inhibits angiotensin II-induced vascular inflammation and remodeling. On the other hand, a plethora of studies suggest that Nox4 also contributes to disease development, especially in situations involving ischemia or fibrosis. In fact, an increasing number of human studies indicate that biosynthesis of Nox4 is upregulated in various diseases including hypertension, cardiac hypertrophy, atherosclerosis, diabetic nephropathy, pulmonary hypertension, and pulmonary fibrosis. In streptozotocin-induced diabetic rats, expression of Nox4 is increased and deletion of Nox4 is reno-protective. Nox4 also contributes to the atherosclerotic phenotype in smooth muscle and potentially mediates cardiac hypertrophy in response to phenylephrine and pressure overload. Compared to wild-type mice, global Nox4 knockout animals showed attenuated liver injury, inflammation, and fibrosis after injury. Cardiac-specific Nox4 knockout mice have less apoptosis, hypertrophy, interstitial fibrosis, and better cardiac function. Nox4 has been shown to have important roles in pulmonary fibrosis as well. In addition, Nox4 in the hypothalamic paraventricular nucleus contributes to hypertension induced by aldosterone and salt in mice, and a small isoform of Nox4 mediates TLR4-induced apoptosis during renal ischemia/reperfusion injury. Other important pathophysiological roles of Nox4 include promoting the loss of bone mass in osteoporosis, contributing to lung vascular permeability induced by *Pseudomonas aeruginosa*, promoting glomerular lesions in a mouse model of diabetic nephropathy, and mediating fibrosis formation in response to TGF-β. Moreover, Nox4 plays an important role in abnormal neuropharmacology by contributing to hypoxia-promoted tumor progression in glioblastoma multiforme, as well as increasing the severity of brain lesions in a model of ischemic stroke.

In certain embodiments, the disclosure relates to uses of a compound as described herein in the production of a medicament for the treatment of kidney and lung fibrosis, cancer, stroke, cardiac hypertrophy, cardiac contractile dysfunction, diabetic nephropathy, arthritis, osteoporosis, peripheral nerve injury, atherosclerosis, aneurysms and pulmonary hypertension.

In certain embodiments, the disclosure relates to methods of treating or preventing cancer comprising administering pharmaceutical composition comprising a compound as described herein optionally in combination with another active ingredient to a subject in need thereof. In further embodiments, the subject is at risk of, exhibiting symptoms of, or diagnosed with cancer.

In certain embodiments, the Nox related disease or condition is a neurological disorder. In certain embodiments, the neurological disorder Alzheimer's disease, Parkinson's disease, Huntington's disease, amyotrophic lateral sclerosis, or multiple sclerosis.

In certain embodiments, the Nox related disease or condition is ischemic injury, ischemia-reperfusion (IR) injury, traumatic brain injury, myocardial infarction (MI), peripheral artery disease, or stroke.

In certain embodiments, the Nox related disease or condition is a cardiovascular disorder, respiratory disorder, metabolism disorder, skin disorder, bone disorder, neuroinflammatory and/or neurodegenerative disorder, kidney disease, reproduction disorder, diseases affecting the eye and/or the lens and/or conditions affecting the inner ear, inflammatory disorder, liver disease, pain, cancer, allergic disorder, traumatisms, septic, hemorrhagic and anaphylactic shock, diseases or disorder of the gastrointestinal system, and angiogenesis.

In certain embodiments, the Nox related condition is selected from cancer, inflammation, a chronic disease of the intestine, atherosclerosis, hypertension, restenosis after angioplasty, myocardial infarction, aortic dissection, hepatic fibrosis, amyotrophic lateral sclerosis, pulmonary hypertension, degenerative brain diseases, allergic airway inflammation, arthritis, kidney and lung fibrosis, brain damage after stroke, cardiac hypertrophy and contractile dysfunction, diabetic nephropathy, osteoporosis, peripheral nerve injury, restenosis after angioplasty, aneurysms, leprechaunism, albuminuria, Barrett's esophagus, asthma, chronic obstructive pulmonary diseases, and cystic fibrosis.

Formulations

Pharmaceutical compositions disclosed herein may be in the form of pharmaceutically acceptable salts, as generally described below. Some preferred, but nonlimiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below). When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group.

Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds. The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Generally, such unit dosages will contain between 1 and 1000 mg, and usually between 5 and 500 mg, of the at least one compound of the disclosure, e.g. about 10, 25, 50, 100, 200, 300 or 400 mg per unit dosage. The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered.

Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more Nox inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al, (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins, zein, shellac, and polysaccharides. Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, arginine, gums or cross linked polymers, such as cross-linked PVP. Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide.

Examples of amphoteric surfactants include sodium N-dodecyl-beta-alanine, sodium N-lauryl-beta-iminodipropionate, myristoamphoacetate, lauryl betaine and lauryl sulfobetaine. If desired, the tablets, beads, granules, or particles may also contain minor amount of nontoxic auxiliary substances such as wetting or emulsifying agents, dyes, pH buffering agents, hypertonic solution of sodium bicarbonate, or preservatives. Typical buffering agents include phosphate, carbonate, and sulfate salts. Examples of buffering agents include $Na_2HPO_4$, $KH_2PO_4$, citric acid, and acetic acid.

The concentration of the Nox inhibitor(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt % of the active material. The compositions described herein can be formulation for modified or controlled release. Examples of controlled release dosage forms include extended release dosage forms, delayed release dosage forms, pulsatile release dosage forms, and combinations thereof. The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form.

The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

Alternatively, extended release formulations can be prepared using osmotic systems or by applying a semi-permeable coating to the dosage form. In the latter case, the desired drug release profile can be achieved by combining low permeable and high permeable coating materials in suitable proportion. The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads. Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose.

Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils. Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine. The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers.

Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins; vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac.

Combinations of different coating materials may also be used. Multi-layer coatings using different polymers may also be applied. The preferred coating weights for particular coating materials may be readily determined by those skilled in the art by evaluating individual release profiles for tablets, beads and granules prepared with different quantities of various coating materials.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

The Nox inhibitors described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

"Adjunctive administration", as used herein, means the Nox inhibitors can be administered in the same dosage form or in separate dosage forms with one or more other active agents. Specific examples of compounds that can be adjunctively administered with the Nox inhibitors include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafmil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof. The additional active agent(s) can be formulated for immediate release, controlled release, or combinations thereof.

Examples

Inhibitors of the NADPH Oxidase, Nox4

A series of novel tertiary sulfonylureas was designed using pharmacophore modeling, synthesized, and evaluated for inhibition of Nox4-dependent signaling. Three potential Nox4 inhibitors were identified with $IC_{50}$ values of 27 μM, 3.7 μM and 0.5 μM in cell-based assays.

At this time, there are no reported X-ray structures of the NADPH oxidases. Without the advantage of 3D structural data of the macromolecular target, a pharmacophore-based approach coupled with energy-based calculations, molecular overlays, and chemical informatics was pursued.

The first iteration of pharmacophore modeling focused on lead identification. Multiple models were generated using the Phase module of Schrödinger Inc. software and scored in search of novel biologically active chemotypes. The subsequent iterations concentrated on lead optimization. The biological data obtained from the leads identified in the first iteration were used to improve the pharmacophore model which was then used to identify more potent compounds.

Strategy I: Multiple pharmacophore models were pursued using a series of compounds as represented in FIG. 1. See Borbély et al. Small-molecule inhibitors of NADPH Oxidase 4. J. Med. Chem., 2010, 53 (18), 6758-6762. Some of the prioritized hits were known antioxidants like robinetin, 2, and catechin, 3 (FIG. 1). Following the biological testing of the selected compounds from these models, compounds were identified that reduce ROS concentration, but apparently through scavenging and not through Nox4 enzyme inhibition.

Figure 2:
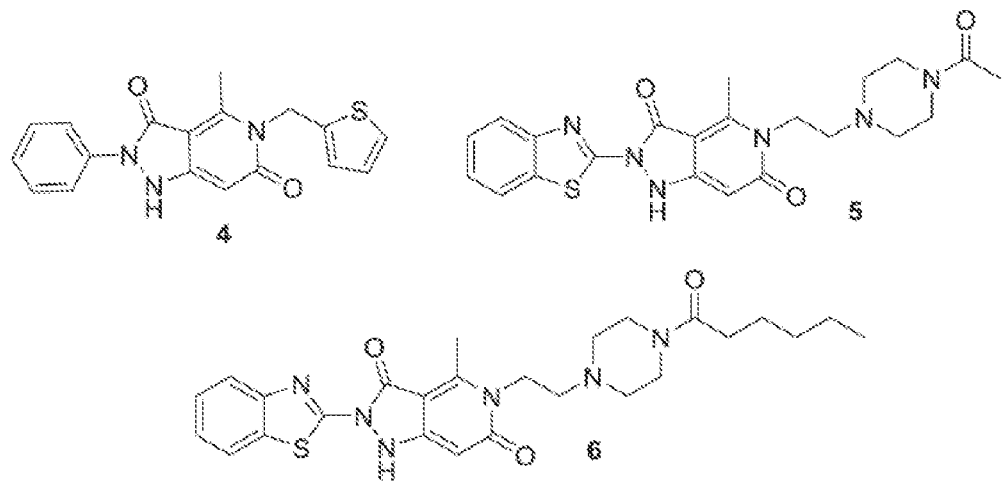
FIG. 2 illustrates compounds.
Figure 3:
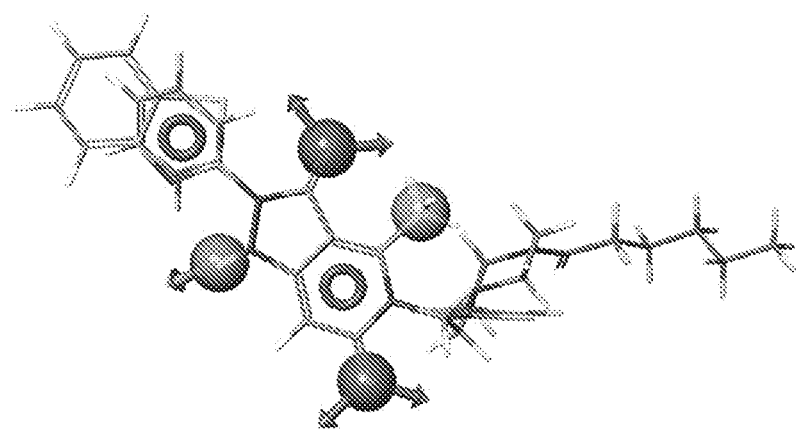
FIG. 3 illustrates compounds 4-6 overlaid with the pharmacophore model, AADHRR.9.
Figure 4:
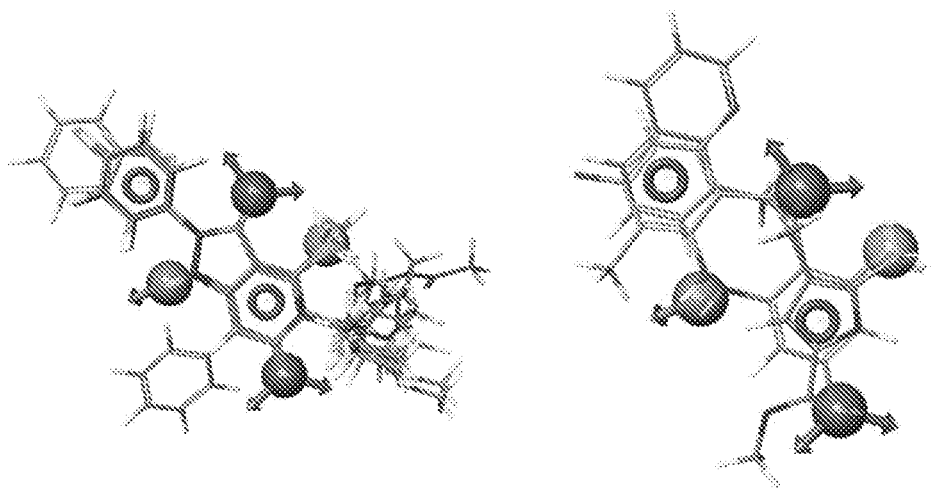
FIG. 4 illustrates a sample of compounds retrieved by the pharmacophore model: those that contain the pyrazolo pyridine scaffold (left), and those do not contain the pyrazolo pyridine scaffold, but fit the pharmacophore model with a high score (right).
Figure 5:
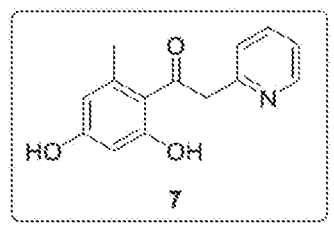
FIG. 5 illustrates compound (7) retrieved by the initial pharmacophore model is displayed along with the pharmacophore model.
Figure 6:
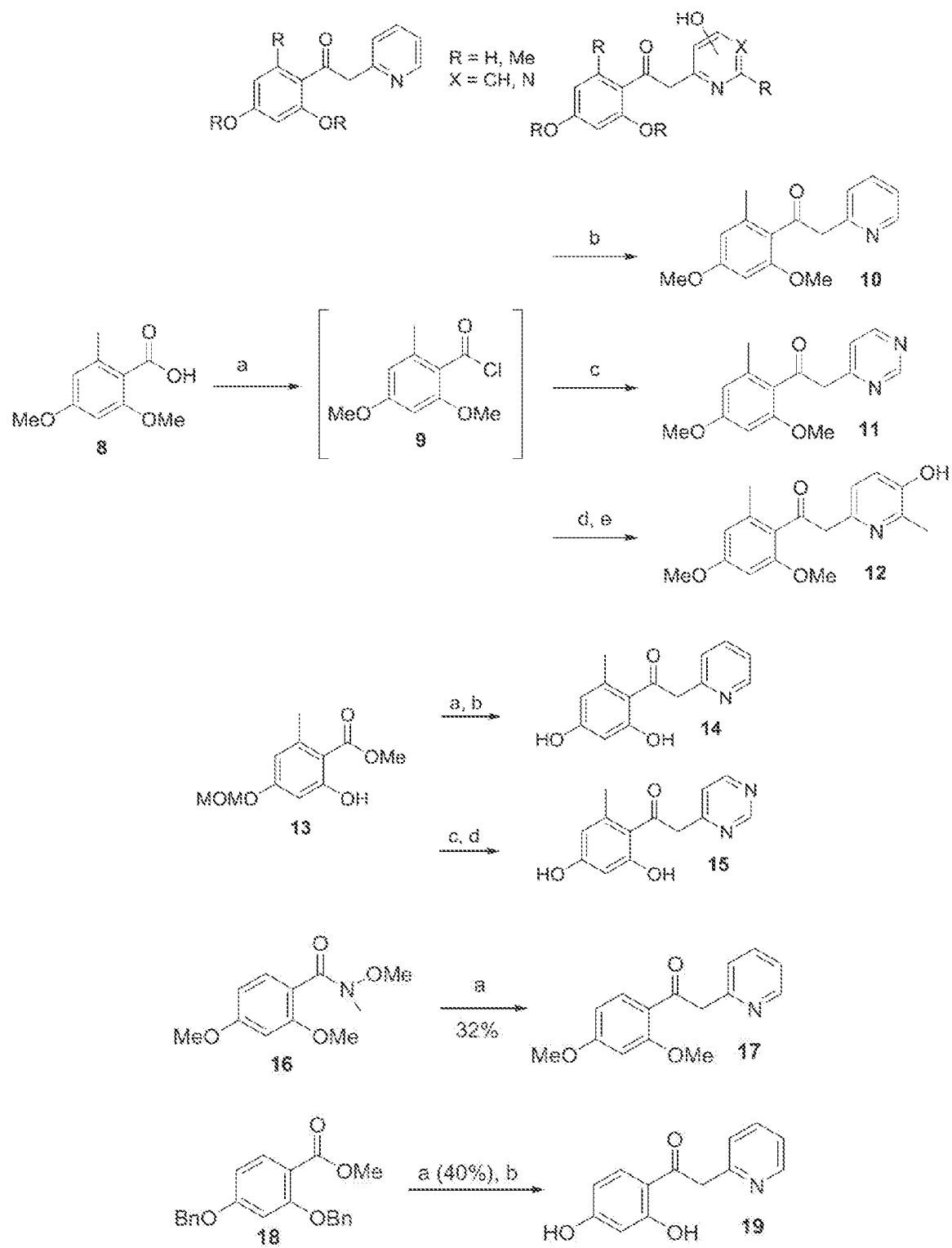
FIG. 6 illustrates acetophenone analogues derived from compound (7) and the synthesis of compounds 10-19. Top scheme reagents and conditions: (a) $SOCl_2$, toluene, 110° C., 4 h; (b) 2-methylpyridine, TEA, THF, LDA, −78° C., 2 h then rt-overnight (65%, 2 steps); (c) 4-methylpyrimidine, TEA, THF, LDA, −78° C., 2 h then rt-overnight (40%, 2 steps); (d) 3-(methoxymethoxy)-2,6-dimethylpyridine, TEA, THF, LDA, −78° C., 2 h then rt-overnight (45%, 2 steps); (e) 3 N HCl (2 equiv.), EtOH, 80° C., 2.5 h (80%). Middle scheme reagents and conditions: (a) 2-methylpyridine, LDA, THF, −78° C., 2 h (52%); (b) 3 N HCl (2 equiv.), EtOH, 80° C., 3 h (81%); (c) 4-methylpyrimidine, LDA, THF, −78° C., 2 h (42%); (d) 3 N HCl (2 equiv.), EtOH, 45° C., 3 h (52%). Bottom scheme reagents and conditions: (a) 2-methylpyridine, n-BuLi, THF, −20° C., 2 h; (b) 10% Pd/C, EtOH, $H_2$ (1 atm), overnight (48%).

Strategy II: A second set of models was developed based on data disclosed in Page et al. Pyrazolo pyridine derivatives as NADPH oxidase inhibitors, U.S. Pat. No. 8,389,518 (2013). Three representative compounds are shown in FIG. 2. A pharmacophore model was developed through the alignment of selected Nox4 inhibitors and subsequently used to retrieve compounds from a 3D-structural database. The three representative compounds are shown overlaid with the pharmacophore model in FIG. 3. A six-feature pharmacophore model, AADHRR.9, is the ninth in a series of models that contain two H-bond acceptors, one H-bond donor, one hydrophobic group, and two aromatic groups. The model retrieved many compounds that contain a pyrazolo-pyridine scaffold (FIG. 4, left). Compounds possessing alternative scaffolds were of interest, as a means to identify active compounds with a lower molecular weight (FIG. 4, right). The first compound (7), retrieved from a commercially available chemical database, is displayed in FIG. 5. To validate the model, a series of related acetophenone derivatives were synthesized and tested (FIG. 6). Gaining access to this series of compounds was initially envisioned through the Weinreb amide of suitably substituted benzoic acids. Unfortunately, steric crowding around the amide functionality precluded nucleophilic addition of the lithiated 2- and 4-methylheterocycles. Therefore, they were prepared from the acid chloride, as other means failed. Thus, commercially available acid 8 was converted to the corresponding acid chloride 9 via treatment with thionyl chloride at 110° C. for 4 h (FIG. 6). The acid chloride was subsequently treated with lithiated 2-methylpyridine, 4-methylpyrimidine, or 3-(methoxymethoxy)-2,6-dimethylpyridine at −78° C. to give the corresponding derivatives 10, 11 and 12, respectively.

Figure 7:
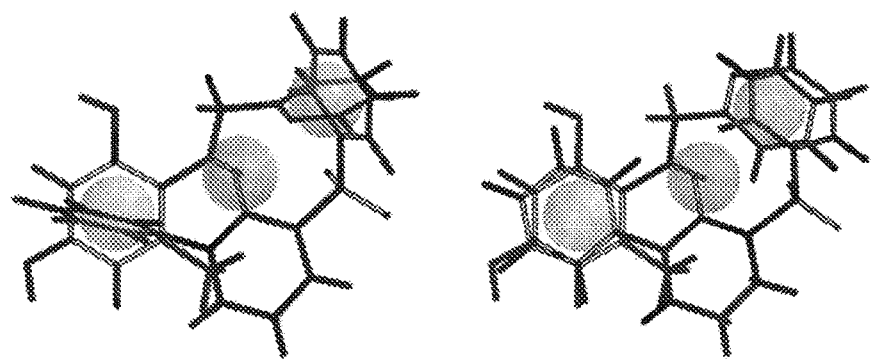
FIG. 7 illustrates a molecular scaffold of the sulfonylurea compounds from the third, modified pharmacophore modeling strategy aligned with the compound in Spartan. The superimposed molecular structures on the left have been energy minimized at the Hartree-Fock level of theory with the 6-31G(d) basis set using the Spartan molecular modeling software package. The molecular structures on the right have the aromatic rings adjusted from the low energy conformation to overlap with the pharmacophore model.

Strategy III: Utilizing the biological assay results obtained from Strategy II, refinement of the pharmacophore model was attempted (FIG. 4, FIG. 5). The inherent scavenging behavior was eliminated through structural modifications of the central region by reducing conjugation and removing of the phenolic functionality. By maintaining the aromatic pharmacophore features in the periphery, changes were systematically made by eliminating the central features one at a time. The aromatic features in the periphery were maintained. Utilizing sulfonylureas was envisioned to link the aromatic regions. This resulted in the model (FIG. 7), which is one of several possible alignments. This modified version has two aromatic regions connected by a sulfonylurea moiety, and the two aromatic rings are orthogonal to the original positions of the aromatic rings in the previous model. Based on the final model, a subset of candidate sulfonylureas (FIG. 7, FIG. 8) were evaluated in biological assays (in vitro), in an effort to validate the revised model and to find a compound for Nox4 inhibition. This model resulted in a series of sulfonylureas (FIG. 8) described herein.

Figure 8:
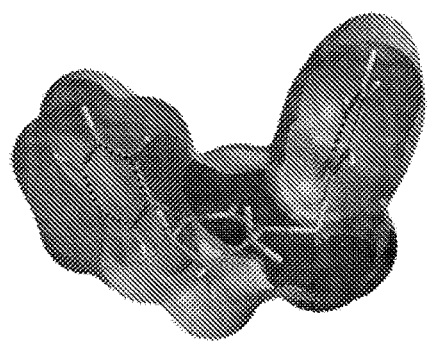
FIG. 8 illustrates three sulfonylureas (23-25) and synthesis. The molecular structure shown on the left is the sulfonylurea scaffold that was energy minimized at the Hartree-Fock level of theory with the 6-31G(d) basis set using the Spartan molecular modeling software package. The electrostatic potential energy surface is displayed, where dark represents the most electronegative regions. Synthesis reagents and conditions: (a) 2-chloroethyl isocyanate or 3-chloropropyl isocyanate, $CH_2Cl_2$, rt (87-89%); (b) i. NaH, ii. 4-methoxy benzenesulfonyl chloride or 4-fluoro benzenesulfonyl chloride (86-88%, 2 steps).
Figure 8:
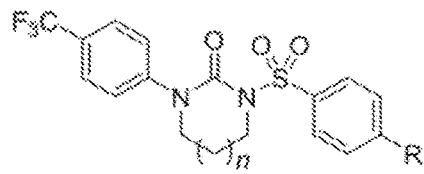
Figure 8:
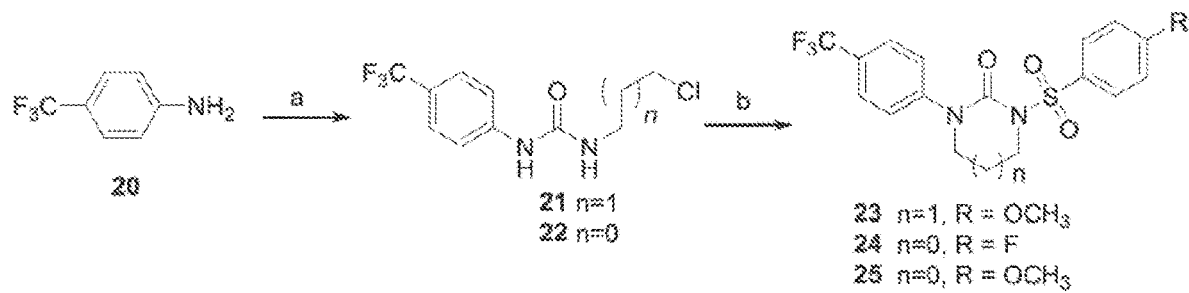

Synthesis of sulfonylurea compounds 23-25 is outlined in FIG. 8. Treatment of 4-trifluoromethyl aniline 20 with 2-chloroethyl isocyanate or with 3-chloropropyl isocyanate resulted in the formation of chlorosubstituted acyclic ureas 21 and 22. Sodium hydride (NaH)-mediated cyclization yielded cyclic urea derivatives, which were subsequently converted into the desired sulfonylurea products 23-25 upon reaction with 4-substituted benzenesulfonyl chlorides.

Biology

The primary products of the Nox enzymes are ROS. Nox enzymes directly produce superoxide, which is quickly converted to hydrogen peroxide. Many organic compounds are able to scavenge superoxide and hydrogen peroxide without affecting enzyme activity; thus, in vitro assays were developed to measure these non-specific effects. Previous strategies for ROS detection using non-specific luminescent or fluorescent probes in cells or in cell-free systems tend to result in false positives. High-throughput screening approaches for monitoring $H_2O_2$ and superoxide have been developed that may represent an effective strategy to test inhibitors of various Nox isoforms. Nevertheless, one can rule out ROS scavenging and focus on the ability to suppress Nox enzyme activity.

Figure 10:
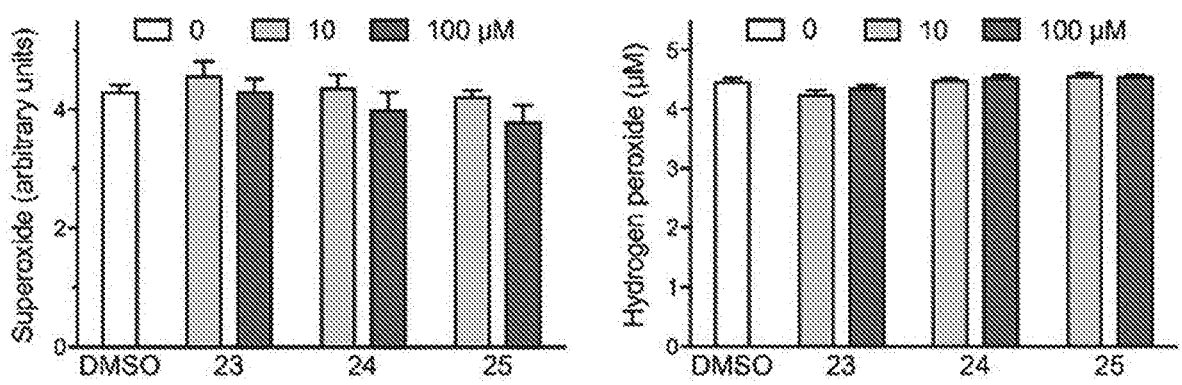
FIG. 10 shows data indicating sulfonylurea compounds minimally scavenge ROS in vitro. ROS scavenging by sulfonylurea compound 23, 24, or 25 was assessed in vitro. Superoxide was generated with xanthine/xanthine oxidase and measured using the cytochrome C assay. In addition, 5 μM hydrogen peroxide was added exogenously and measured using the Amplex Red™ assay. ROS were measured in the presence of indicated concentrations of each compound or DMSO solvent. Bars represent means±SEM of 4 (superoxide) or 3 (hydrogen peroxide) independent experiments. Differences between DMSO and sulfonylurea compounds are not significant.

To assess ROS scavenging, the consumption of superoxide, generated by xanthine/xanthine oxidase, or of exogenous hydrogen peroxide, was measured by increasing concentrations of the compounds of interest. As shown in FIG. 10, compounds 23, 24, and 25 had no effect on superoxide and hydrogen peroxide in vitro at concentrations up to 100 μM.

Figure 11:
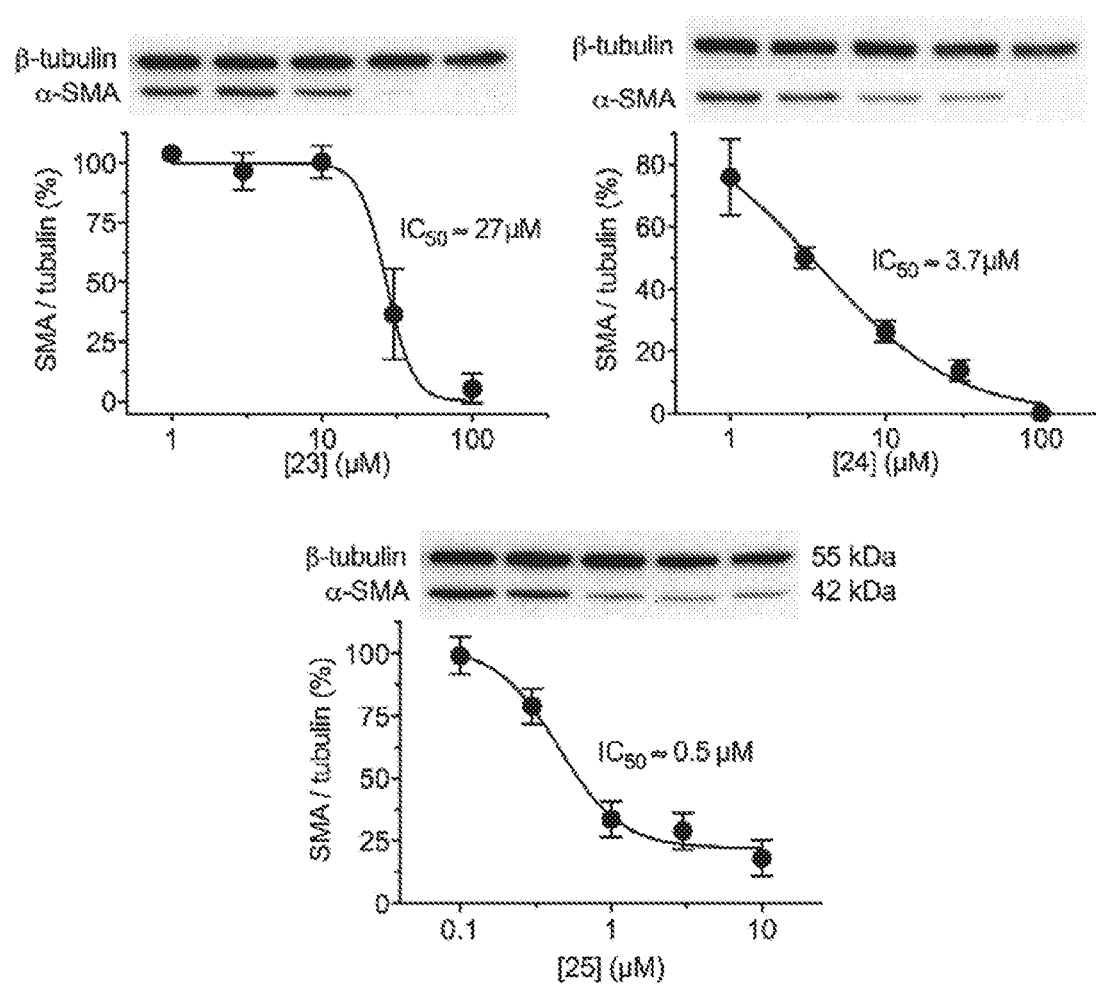
FIG. 11 shows data indicating sulfonylurea compounds inhibit Nox4-dependent signaling in cells. Human aortic smooth muscle cells in culture were incubated with indicated concentrations of compound 23, 24, or 25 and stimulated with 2 ng/ml TGF-β for 24 h to induce a Nox4-dependent upregulation of smooth muscle alpha-actin (α-SMA). Protein expression was measured by Western blotting and normalized to β-tubulin. In the absence of inhibitor, α-SMA induction by TGF-β was maximal (100%). All three sulfonylurea compounds reduced α-SMA expression, allowing determination of each $IC_{50}$ by non-linear regression, as indicated.

To test the biological effectiveness of compounds that did not scavenge ROS, upregulation of vascular smooth muscle alpha actin (α-SMA) was measured by TGF-β treatment of human aortic smooth muscle cells (HASMCs) in culture. This effect of TGF-β has previously been shown to be Nox4-dependent. Cells were pretreated with a candidate inhibitor 30 min before exposure to TGF-β and harvested after 24 h. Actin expression was measured by western blotting with a specific antibody. As shown in FIG. 11, compounds 23, 24 and 25 were capable of profoundly inhibiting Nox4-dependent signaling. These results suggest that sulfonylurea compounds may be direct Nox4 inhibitors.

TGF-β is known to significantly upregulate Nox4 expression in smooth muscle cells by 24 h. To ensure that sulfonylurea compounds did not exert their effects by preventing Nox4 upregulation, Nox4 mRNA was measured in cells treated as in FIG. 11, using a qPCR assay. In control cells stimulated with TGF-β alone, Nox4 mRNA was upregulated. Furthermore, preincubation with compounds 23, 24 and 25 in the same range of concentrations as in FIG. 11, did not affect Nox4 expression.

To rule out a possible toxic effect of these compounds in cultured cells, cell viability was measured using a commercial mammalian cell live/dead assay. Stimulation with TGF-β alone had no effect on cell viability (99±0.61%, P=NS, n=4). However, cell viability was slightly reduced by preincubation with the highest concentration (100 μM) of compound 23 (92±3.09% viability, P<0.05, n=6), but not 24 (100 μM, 100±0.97% viability, P=NS, n=6) or 25 (10 μM, 97±2.50% viability, P=NS, n=6).

Synthetic Procedures 1-(2,4-Dimethoxy-6-methylphenyl)-2-(pyridin-2-yl) ethan-1-one (10) and 1-(2,4-dimethoxy-6-methylphenyl)-2-(pyrimidin-4-yl)ethan-1-one (11)

Thionyl chloride (79 mg, 0.663 mmol, 0.048 mL, 1.3 equiv.) was added dropwise to 2,4-dimethoxy-6-methylbenzoic acid (8, 100 mg, 0.510 mmol) dissolved in anhydrous toluene (5 mL) at rt in a two-neck, 10 mL RBF equipped with a condenser. The solution was heated to reflux for 4 h. The solvent was evaporated under vacuum, and the product (9) was used in the next step without purification.

The acyl chloride (9) was dissolved in dry THF (3 mL), cooled to −78° C., and treated with triethylamine (0.142 mL, 1.02 mmol, 2 equiv.) with stirring. In a separate RBF, dry THF (3 mL) was added followed by diisopropylamine (0.16 mL, 1.121 mmol, 2.2 equiv.). This solution was cooled to −78° C. and treated with n-BuLi (0.67 mL, 1.070 mmol, 2.1 equiv.) and stirred for 10 min. The 2-methylpyridine (104 mg, 0.111 mL, 1.12 mmol, 2.2 equiv.) was added dropwise. After 30 min, the solution of the acid chloride was added via syringe to the lithiated 2-methylpyridine solution. The yellow solution was kept at −78° C. and allowed to warm slowly to rt overnight. The solvent was removed under vacuum. Dichloromethane (10 mL) was added and washed with water (5 mL). The organic layer was dried over $MgSO_4$ and concentrated. The residue was purified on silica (1% MeOH:DCM) to give the product.

Compound 10: Yield 65%, 2 steps, 77:23 mixture of keto:enol tautomers; $^1$H NMR (400 MHz, $CDCl_3$, major isomer) δ 8.55 (dd, J=4.0, 0.8 Hz, 1H), 7.65 (dt, J=8.0, 2.0 Hz, 1H), 7.30 (d, J=8.0 Hz, 1H), 7.17 (dt, J=6.0, 0.8 Hz, 1H), 6.30 (s, 2H), 4.33 (s, 2H), 3.83 (s, 3H), 3.82 (s, 3H), 2.17 (s, 3H); $^{13}$C NMR (100 MHz, $CDCl_3$) δ 203.0, 161.4, 158.5, 155.4, 149.2, 144.1, 138.6, 136.4, 124.4, 121.7, 118.3, 107.3, 95.9, 55.6, 55.3, 53.8, 20.1; FTIR (neat): 2934, 2839, 1688, 1594, 1459, 1320, 1199, 1150, 1093, 808, 751, 620 cm−1; MS (ESI) m/z 272 [M+H]+.

Compound 11: Yield 40%, 2 steps, 55:45 mixture of keto:enol tautomers; $^1$H NMR (400 MHz, $CDCl_3$, major isomer) δ 9.15 (bs, 1H), 8.67 (d, J=4.8 Hz, 1H), 7.35 (d, J=4.4 Hz, 1H), 6.31 (m, 1H), 4.29 (s, 2H), 3.82 (s, 6H), 2.24 (s, 3H); $^{13}$C NMR (100 MHz, $CDCl_3$) δ 200.9, 164.2, 161.8, 158.8, 156.6, 154.3, 139.3, 121.9, 119.7, 107.6, 95.9, 55.6, 55.4, 53.1, 20.3; FTIR (neat): 2997, 2921, 2842, 1629, 1577, 1466, 1316, 1200, 1000, 884, 744, 649 cm−1; MS (ESI) m/z 273 [M+H]+.

1-(2,4-Dimethoxy-6-methylphenyl)-2-(5-hydroxy-6-methylpyridin-2-yl)ethan-1-one (12)

To a stirred solution of the 2,6-dimethylpyridin-3-ol (500 mg, 4.06 mmol) in DMF (15 mL) in a 50 mL flame-dried RBF, $K_2CO_3$ (0.617 g, 4.47 mmol) and MOM-Cl (0.37 mL, 4.87 mmol) were added successively. The solution was stirred at RT overnight. Water (30 mL) was added and the reaction mixture extracted with EtOAc (2×20 mL). The organic layer was washed with cold water (2×30 mL) and brine (30 mL) and dried over magnesium sulfate and concentrated under reduced pressure.

Thionyl chloride (79 mg, 0.663 mmol, 0.048 mL, 1.3 equiv.) was added dropwise to 2,4-dimethoxy-6-methylbenzoic acid (8, 100 mg, 0.510 mmol) dissolved in anhydrous toluene (5 mL) at rt in a two-neck, 10 mL RBF equipped with a condenser. The solution was heated to reflux for 4 h. The solvent was evaporated under vacuum, and the product (9) was used in the next step without purification.

The acyl chloride (9) was dissolved in dry THF (3 mL), cooled to −78° C., and treated with triethylamine (0.142 mL, 1.09 mmol, 2 equiv.) with stirring. In a separate RBF, dry THF (3 mL) was added followed by DIA (0.16 mL, 1.12 mmol, 2.2 equiv.). This solution was cooled to −78° C. and treated with n-BuLi (0.73 mL, 1.121 mmol, 2.2 equiv.) and stirred for 10 min. The MOM-protected pyridine (179 mg, 1.07 mmol, 2.1 equiv.) was added dropwise. After 30 min, the acid chloride solution was added dropwise. The yellow solution was kept at −78° C. and allowed to warm slowly to rt overnight. The solvent was removed under vacuum, and dichloromethane (10 mL) was added and washed with water (10 mL). The organic layer was dried over MgSO$_4$ and concentrated. The residue was purified on silica (2% MeOH:DCM) to give the MOM ether as a yellow solid.

A solution of the MOM ether (50 mg, 0.145 mmol), 3 M HCl (0.097 mL, 0.290 mmol) in EtOH (2 mL) was stirred at 80° C. After the reaction was completed (monitored by TLC), the organic solvent was directly removed under reduced pressure. The residue was taken up in water (1 mL) and the pH adjusted to 6 using sodium bicarbonate solution (1 M). The product was extracted with dichloromethane (3×5 mL) and dried and concentrated. Further purification was achieved on silica with 40% (3:1 EtOH in ethyl acetate)/hexane.

Compound 12: Yield 80%; 63:27 mixture of keto-enol tautomers; $_1$H NMR (400 MHz, DMSO-d6, major isomer) δ 9.54 (s, 1H), 7.00 (d, J=8 Hz, 1H), 6.91 (d, J=8.0 Hz, 1H), 6.44 (d, J=2.0 Hz, 1H), 6.37 (d, J=2.0 Hz, 1H), 4.10 (s, 2H), 3.80 (s, 3H), 3.75 (s, 3H), 2.29 (s, 3H), 2.16 (s, 3H); $^{13}$C NMR (100 MHz, DMSO-d6) δ 203.1, 161.1, 158.3, 149.7, 147.2, 143.3, 138.0, 123.8, 122.4, 122.3, 107.9, 96.3, 56.2, 55.6, 48.9, 23.3, 19.8; FTIR (neat): 2933, 2836, 1575, 1457, 1359, 1281, 1197, 1045, 949, 806, 618 cm−1; MS (ESI) m/z 302 [M+H]+.

1-(2,4-Dihydroxy-6-methylphenyl)-2-(pyridin-2-yl)ethan-1-one (14) and 1-(2,4-dihydroxy-6-methylphenyl)-2-(pyrimidin-4-yl)ethan-1-one (15)

To an ice-cooled solution of ethyl 2,4-dihydroxy-6-methylbenzoate (300 mg, 1.529 mmol) in dichloromethane (10 mL), DIPEA (0.401 mL, 296 mg, 2.29 mmol) and MOM-Cl (0.116 mL, 123 mg, 1.59 mmol) were added successively. The solution was stirred at rt for 4 h. Saturated aqueous NH$_4$Cl (15 mL) was added, and the reaction mixture was extracted with dichloromethane (3×15 mL). The organic layer was washed with water and brine and dried over magnesium sulfate and concentrated under reduced pressure. The off-white, solid residue was purified by flash chromatography to afford the MOM-ether (13) as a viscous liquid (silica, 40% EtOAc: hexanes).

Compound 13: Yield 80%; $^1$H NMR (400 MHz, CDCl$_3$) δ 11.76 (s, 1H), 6.49 (d, J=2.4 Hz, 1H), 6.38 (dd, J=2.4, 0.8 Hz, 1H), 5.17 (s, 2H), 4.41 (q, J=7.2 Hz, 2H), 3.46 (s, 3H), 2.52 (s, 3H), 1.41 (t, J=7.2 Hz, 3H); $^{13}$C NMR (100 MHz, CDCl$_3$) δ 171.6, 165.2, 161.3, 143.3, 111.8, 106.4, 101.5, 93.8, 61.32, 56.3, 24.5, 14.2; FTIR (neat): 2985, 2938, 2828, 1613, 1575, 1398, 1263, 1217, 1022, 926, 866 cm−1.

In a RBF, dry THF (3 mL) was added followed by DIA (0.158 mL, 0.397 mL, 2.78 mmol, 4.2 equiv.). This solution was cooled to −78° C. and treated with n-BuLi (1.669 mL, 2.72 mmol, 4.1 equiv., 1.6 M in hexane) and stirred for 10 min. To this solution, 2-methylpyridine (0.262 mL, 247 mg, 2.65 mmol, 4 equiv.) was added dropwise. After 30 min, a solution of methyl 2-hydroxy-4-(methoxymethoxy)-6-methylbenzoate (13, 150 mg, 0.663 mmol) was added dropwise to the pyridine solution. The yellow solution was kept at −78° C. and allowed to warm to rt over 2 h. The solvent was removed under vacuum, and dichloromethane (10 mL) was added and washed with water (5 mL). The organic layer was dried over MgSO$_4$ and concentrated. The residue was purified on silica (2% MeOH:DCM) to give the MOM-ether as a yellow solid.

A solution of the MOM-ether (60 mg, 0.209 mmol) and 3 M HCl (0.139 mL, 0.418 mmol) in EtOH (4 mL) was stirred at 80° C. After the reaction was completed (monitored by TLC), the solvent was removed under reduced pressure. The residue was taken up in water (1 mL) and the pH adjusted to 6 using sodium bicarbonate solution (1 M), extracted with dichloromethane (3×5 mL), dried and concentrated. Further purification was achieved on a flash column with 10 to 30% (1:3 ethanol in ethyl acetate)/hexane.

Compound 14: Yield 81%; 80:20 mixture of keto-enol tautomers; $^1$H NMR (400 MHz, DMSO-d6, major isomer) δ 10.16 (bs, 1H), 9.65 (s, 1H), 8.45 (d, J=4.4 Hz, 1H), 7.71 (dt, J=7.6, 2.0 Hz, 1H), 7.26-7.21 (m, 2H), 6.18 (d, J=2.0 Hz, 1H), 6.06 (d, J=2.0 Hz, 1H), 4.28 (s, 2H), 2.01 (s, 3H); $^{13}$C NMR (100 MHz, DMSO-d6) δ 202.8, 159.8, 157.7, 156.5, 149.3, 138.9, 136.7, 124.7, 122.1, 120.2, 109.6, 100.6, 53.5, 20.5; FTIR (neat): 2923, 2763, 1592, 1570, 1442, 1375, 1214, 1189, 973, 844, 723, 622 cm−1; MS (ESI) m/z 244 [M+H]+.

Compound 15: Yield 52%; 66:24 mixture of keto-enol tautomers; $^1$H NMR (400 MHz, DMSO-d6, major isomer) δ 10.2 (s, 1H), 9.74 (s, 1H), 9.07 (d, J=1.6 Hz, 1H), 8.71 (d, J=5.2 Hz, 1H), 7.43 (dd, J=4.8, 1.2 Hz, 1H), 6.20 (d, J=2.0 Hz, 1H), 6.10 (d, J=2.0 Hz, 1H), 4.32 (s, 2H), 2.08 (s, 3H); $^{13}$C NMR (100 MHz, DMSO-d6) δ 201.0, 165.1, 160.2, 158.6, 158.2, 157.1, 139.4, 122.7, 119.6, 109.8, 100.6, 52.9, 20.8; FTIR (neat): 3082, 2923, 1605, 1548, 1434, 1350, 1248, 1159, 1051, 982, 820, 690 cm−1; MS (ESI) m/z 245 [M+H]+.

1-(2,4-Dimethoxyphenyl)-2-(pyridin-2-yl)ethan-1-one (17)

In an oven dried 100 mL round-bottom flask was placed 2,4-dimethoxybenzoic acid (1.0 g, 5.49 mmol) and anhydrous dichloromethane (45 mL). The solution was stirred at rt and treated with 1-methylpiperidine (3.35 mL, 27 mmol). After stirring for 10 min the solution was cooled to 0° C. and pivaloyl chloride (0.79 g, 0.81 mL, 6.59 mmol) was added via syringe dropwise. The solution was stirred for 2 h. N,O-Dimethyl hydroxylamine hydrochloride (0.803 g, 8.23 mmol) was added, and the mixture was stirred at room temperature for 24 h. The yellow solution was poured into HCl (80 mL, 1 M). The organic layer was sequentially washed with saturated NaHCO3 and brine (80 mL) and dried over MgSO$_4$. After concentration, the yellow oil was dried under vacuum to afford the amide (16) as a white solid.

Compound 16: Yield 80%; $^1$H NMR (400 MHz, CDCl$_3$) δ 7.19 (d, J=8.4 Hz, 1H), 6.47-6.43 (m, 2H), 3.78 (s, 6H), 3.55 (bs, 3H), 3.23 (bs, 3H); $^{13}$C NMR (100 MHz, CDCl$_3$) δ 161.8, 157.3, 129.0, 117.7, 104.3, 98.6, 60.9, 55.7, 55.4; FTIR (neat): 2964, 2935, 1642, 1606, 1513, 1311, 1289, 1118, 988, 938 cm−1.

Dry THF (2 mL) and 2-methylpyridine (41 mg, 0.44 mmol) were added to a 10 mL round-bottom flask and cooled to −78° C. To this, n-BuLi (277 μL, 0.444 mmol) was added dropwise. A two-neck, round-bottom flask was charged with dry THF (2 mL) and N-2,4-trimethoxy-N-methylbenzamide (16, 100 mg, 0.444 mmol) was added. The solution was cooled to −78° C. with stirring. After 30 min, the lithiated 2-methylpyridine solution was added dropwise over 10 min via syringe pump. The reaction was stirred at −78° C. for 2 h and warmed to 0° C. Water was added to the reaction, and the product was extracted with EtOAc (2×5 mL). The combined organic layers were washed with brine, dried and concentrated. The residue was purified by flash chromatography by eluting with 10 to 20% EtOAc in hexanes to afford the ketone (17) in 32% yield.

Compound 17: Yield 32%; 88:12 mixture of keto: enol tautomers; $^1$H NMR (400 MHz, CDCl$_3$, major isomer) δ

8.48 (dd, J=4.8 Hz, 0.8 Hz, 1H), 7.83 (d, J=8.8 Hz, 1H), 7.56 (dt, J=7.6 Hz, 2.0 Hz, 1H), 7.17 (d, J=8.0 Hz, 1H), 7.08 (ddd, J=7.6, 4.8 Hz, 0.8 Hz, 1H), 6.46 (dd, J=8.8, 2.4 Hz, 1H), 6.36 (d, J=2.4 Hz, 1H), 4.43 (s, 2H), 3.83 (s, 3H), 3.78 (s, 3H); $^{13}$C NMR (100 MHz, CDCl$_3$) δ 196.4, 164.7, 161.0, 156.5, 149.3, 136.2, 133.2, 124.3, 121.5, 120.7, 105.3, 98.3, 55.6, 55.5, 52.8; FTIR (neat): 3006, 2940, 2838, 1661, 1592, 1502, 1435, 1258, 1110, 1024, 824, 750, 639 cm−1; MS (ESI) m/z 258 [M+H]+.

1-(2,4-Dihydroxyphenyl)-2-(pyridin-2-yl)ethan-1-one (19)

Methyl 2,4-dihydroxybenzoate (3 g, 17.83 mmol), benzylbromide (6.71 g, 4.67 mL, 39.3 mmol), and potassium carbonate (5.4 g, 39.3 mmol) were added to acetonitrile (120 mL) and were stirred under argon at 60° C. for 48 h. After 24 h an additional 0.5 equiv. BnBr and 1 equiv. K$_2$CO$_3$ were added. The reaction mixture was filtered through Celite, and the solvent removed under vacuum. The resulting oil was purified by flash chromatography (silica: 10% EtOAc: hexanes) to give the product (18) as a white solid (4.8 g, 77%).

Compound 18: Yield 77%; $^1$H NMR (400 MHz, CDCl$_3$) δ 7.81 (d, J=8.4 Hz, 1H), 7.43-7.41 (m, 2H), 7.33-7.23 (m, 8H), 6.53-6.49 (m, 2H), 5.06 (s, 2H), 4.99 (s, 2H), 3.79 (s, 3H); $^{13}$C NMR (100 MHz, CDCl$_3$) δ 136.6, 136.1, 133.9, 128.7, 128.5, 128.2, 127.7, 127.5, 126.7, 113.2, 113.1, 106.1, 106.0, 101.5, 101.4, 70.5, 70.2, 51.7; FTIR (neat): 3066, 3035, 2835, 1724, 1604, 1505, 1378, 1188, 1129, 1008, 811 cm−1.

Dry THF (9 mL) and 2-methylpyridine (167 mg, 0.178 mL, 1.79 mmol) were added to a 25 mL round-bottom flask and cooled to −78° C. To this, n-BuLi (1.12 mL, 1.79 mmol) was added dropwise. A 50 mL, two-neck round-bottom flask was charged with dry THF (9 mL) and methyl 2,4-bis (benzyloxy)benzoate (18, 250 mg, 0.78 mmol) was added and cooled to −78° C. with stirring. After 30 min, the lithiated 2-methylpyridine solution was added dropwise over 2 min. The reaction was stirred at −78° C. for 10 min and water was added. After warming to rt, the product was extracted with EtOAc and the aqueous layer was back-extracted with EtOAc (2×10 mL). The combined organic layers were dried and concentrated. The bisbenzyl product was purified by flash chromatography (40%).

The bisbenzyl ketone (120 mg, 0.293 mmol) was dissolved in EtOH and 10% Pd/C (15.5 mg) was added. The mixture was stirred at rt under 1 atmosphere of H$_2$ overnight. The reaction mixture was filtered and purified by column chromatography by eluting with 1-2% MeOH in dichloromethane to give the product as a yellow solid (48%).

Compound 19: Yield 48%; $^1$H NMR (400 MHz, DMSO-d6,) δ 12.4 (s, 1H), 10.14 (bs, 1H), 8.46 (m, 1H), 7.71 (dd, J=9.2, 2.4 Hz, 1H), 7.64-7.59 (m, 1H), 7.25 (d, J=7.6 Hz, 1H), 7.15-7.12 (m, 1H), 6.32-6.30 (m, 1H), 6.24-6.23 (m, 1H), 4.33 (s, 2H); $^{13}$C NMR (100 MHz, DMSO-d6) δ 200.8, 165.5, 165.4, 155.32, 149.5, 136.7, 133.2, 124.2, 122.0, 112.6, 108.6, 103.1, 47.7; FTIR (neat): 2924, 2870, 2755, 1613, 1587, 1415, 1344, 1227, 1124, 945, 842, 761 cm−1; MS (ESI) m/z 230 [M+H]+.

1-(2-Chloroethyl)-3-(4-(trifluoromethyl)phenyl)urea (21) and 1-(3-Chloropropyl)-3-(4-(trifluoromethyl) phenyl)urea (22)

A 50 mL round-bottom flask was charged with a solution of 4-trifluoromethyl aniline (20, 1.61 g, 10 mmol, 1.0 equiv.) in CH$_2$Cl$_2$ (20 mL). 2-Chloroethyl isocyanate or 3-chloropropyl isocyanate (10 mmol, 1.0 equiv.) was added, and the reaction was stirred at rt for 72 h. The white precipitate was filtered, washed with CH$_2$Cl$^2$ (10 mL), and dried under high vacuum. The compound was used in subsequent steps without any further purification.

Compound 21 was synthesized as described in the general procedure using 3-chloropropyl isocyanate (1.2 g, 10 mmol, 1.0 equiv). The desired product was isolated as a white solid (2.51 g, 89% yield). The crude solid was used without further purification. $^1$H NMR (400 MHz, DMSO-d6): δ 8.92 (s, 1H), 7.60-7.53 (m, 4H), 6.44-6.42 (t, J=4.0 Hz, 1H), 3.68-3.65 (t, J1=8.0, 4.0 Hz, 2H), 3.25-3.20 (m, 2H), 1.93-1.86 (m, 2H). $^{13}$C NMR (100 MHz, DMSO-d6): 155.4, 144.7, 126.5, 126.3, 123.8, 121.6, 121.3, 117.7, 43.5, 37.1, 33.0. FTIR (neat): 3321, 2969, 1695, 1637, 1596, 1557, 1522, 1409, 1310, 1230, 1180, 1156, 1062, 1013 cm−1.

Compound 22 was synthesized as described in the general procedure using 2-chloroethyl isocyanate (1.05 g, 10 mmol, 1.0 equiv.). The desired product was isolated as a white solid (2.32 g, 87% yield). The crude solid was used without further purification. $^1$H NMR (400 MHz, DMSO-d6): δ 9.11 (s, 1H), 7.61-7.55 (m, 4H), 6.56 (t, 1H), 3.68-3.65 (t, J=8.0 Hz, 2H), 3.46-3.41 (m, 2H). $^{13}$C NMR (100 MHz, DMSO-d6): δ 155.2, 144.5, 126.4, 126.4, 123.7, 121.8, 121.5, 117.8, 44.7, 41.7. FTIR (neat): 3379, 2970, 2929, 1737, 1650, 1598, 1562, 1408, 1323, 1243, 1157, 1064, 1013 cm−1.

1-((4-Methoxyphenyl)sulfonyl)-3-(4-(trifluoromethyl)phenyl)-tetrahydropyrimidin-2(1H)-one (23), 1-((4-Fluorophenyl)sulfonyl)-3-(4-(trifluoromethyl) phenyl)-tetrahydropyrimidin-2(1H)-one (24), and 1-((4-Methoxyphenyl)sulfonyl)-3-(4-(trifluoromethyl)phenyl)-imidazolidin-2-one (25)

A round bottom flask (10 mL) equipped with a magnetic stir bar was charged with a solution of the acyclic urea (0.25 mmol, 1.0 equiv.) in THF (2 mL). The solution was cooled to 0° C. for 15 min. NaH (30 mg, 0.75 mmol, 3.0 equiv., 60% suspension in oil) was slowly added. The reaction was stirred for 15 min at 0° C. and allowed to warm to rt with stirring for 12 h. The appropriate arylsulfonyl chloride (0.28 mmol, 1.1 equiv.) was added, and the reaction was stirred at rt for an additional 4 h. The reaction mixture was poured into a separatory funnel containing ethyl acetate and 1 M HCl (10 mL each). The layers were separated. The organic layer was washed with distilled H2O (2×10 mL) and dried over anhydrous Na2SO4. The solvent was removed under vacuum. The crude product was purified using silica gel flash column chromatography. Gradient elution from 20 to 40% ethyl acetate in hexanes furnished the purified products as white crystalline solids.

Compound 23 was synthesized as described in the general procedure using acyclic urea 21 (70 mg, 0.25 mmol, 1.0 equiv.) and 4-methoxybenzenesulfonyl chloride (58 mg, 0.28 mmol, 1.1 equiv). The desired cyclic sulfonylurea 23 was isolated as a white crystalline solid (88 mg, 85% overall yield). $^1$H NMR (400 MHz, CDCl$_3$) δ 8.02-7.93 (m, 2H), 7.56 (t, J=12.6 Hz, 2H), 7.36 (d, J=8.3 Hz, 2H), 6.99-6.93 (m, 2H), 4.14-4.04 (m, 2H), 3.86 (d, J=3.4 Hz, 3H), 3.70 (dd, J=13.0, 7.0 Hz, 2H), 2.29-2.21 (m, 2H). $^{13}$C NMR (100 MHz, CDCl$_3$): δ 163.6, 151.0, 145.4, 145.3, 131.2, 130.9, 126.2, 125.1, 122.3, 113.9, 55.7, 49.1, 45.4, 22.9. FTIR (neat): 2924, 2855, 1739, 1667, 1595, 1578, 1519, 1497, 1476, 1422, 1324, 1283, 1265, 1175, 1107, 1092, 1065, 1019 cm−1; HRESIMS m/z 415.0936 (M+H)+ (calcd for C18H18F3N2O4S, 415.0939).

Compound 24 was synthesized as described in the general procedure using acyclic urea 22 (70 mg, 0.25 mmole, 1.0 equiv.) and 4-fluorobenzenesulfonyl chloride (54 mg, 0.28 mmol, 1.1 equiv.). The desired cyclic sulfonylurea 24 was isolated as a white crystalline solid (91 mg, 90% overall yield). $^1$H NMR (400 MHz, CDCl$_3$) δ 8.04 (ddd, J=8.1, 5.1, 2.5 Hz, 2H), 7.58 (d, J=8.5 Hz, 2H), 7.34 (d, J=8.3 Hz, 2H), 7.20-7.12 (m, 2H), 4.15-4.06 (m, 2H), 3.72 (dd, J=11.6, 5.8 Hz, 2H), 2.32-2.20 (m, 2H). $^{13}$C NMR (100 MHz, CDCl$_3$): δ 166.8, 164.3, 150.8, 145.0, 135.6, 131.6, 128.8, 126.2, 125.1, 122.4, 116.1, 49.0, 45.5, 22.8. FTIR (neat): 2922, 2853, 1668, 1614, 1591, 1518, 1491, 1476, 1426, 1412, 1328, 1287, 1239, 1206, 1225, 1123, 1175, 1155, 1086, 1035, 1011 cm−1; HRESIMS m/z 403.0735 (M+H)+ (calcd for C17H15F4N2O3S, 403.0740).

Compound 25 was synthesized as described in the general procedure from acyclic urea 22 (67 mg, 0.25 mmol, 1.0 equiv.) and 4-methoxybenzenesulfonyl chloride (58.0 mg, 0.28 mmol, 1.1 equiv.). The desired cyclic sulfonylurea 25 was isolated as a white crystalline solid (80 mg, 80% overall yield). $^1$H NMR (400 MHz, CDCl$^3$): δ 8.072 (d, J=2.00, 8.00 Hz, 2H), 7.60 (m, 4H), 7.05-7.02 (m, 2H), 4.08-4.04 (m, 2H), 3.82 (m, 5H). $^{13}$C NMR (100 MHz, CDCl$_3$): δ 182.8, 164.2, 151.7, 141.5, 130.7, 129.1, 126.2, 122.6, 117.9, 114.3, 55.7, 42.1, 41.0, 30.9. FTIR (neat): 2908, 2849, 1719, 1617, 1593, 1576, 1524, 1496, 1467, 1397, 1358, 1313, 1296, 1260, 1178, 1153, 1089, 1069, 1022 cm−1; HRESIMS m/z 423.0600 (M+Na)+ (calcd for C17H15F3N2O4SNa, 423.0602).

Superoxide Scavenging Assay

An assay was developed based on the measurement of superoxide-dependent changes in cytochrome C absorbance at 550 nm. Briefly, superoxide was generated in vitro in phosphate buffered saline solution, using hypoxanthine (100 μM)/xanthine oxidase (6×10$^3$ U/mL) in the presence of catalase (200 U/mL) to eliminate H2O2. Compounds under study were added at various concentrations (1-100 μM) and remaining superoxide was measured with cytochrome C (46 μM). Superoxide dismutase (575 U/mL) was used as a positive control in separate samples measured at the same time. Following a 1 min stabilization period, absorbance was measured at 550 nm in a microplate reader (Biotek), using a kinetic program (1 read/min) for 15 min. The linear slope representing the rate of superoxide production was used to calculate the percentage of superoxide scavenging.

Hydrogen Peroxide Scavenging Assay

Hydrogen peroxide was measured in vitro, using an Amplex Red™ assay kit (Invitrogen), according to the manufacturer's instructions. This assay measures the oxidation of Amplex Red™ (10-acetyl-3,7-dihydroxyphenoxazine) to fluorescent resorufin in the presence of horseradish peroxidase. Briefly, H$_2$O$_2$ (5 mM) was added to various concentrations (1-100 μM) of the compounds under study in reaction buffer. After an incubation of 5 min, Amplex Red™ was added to measure remaining H$_2$O$_2$. Reactions were incubated for 30 min at room temperature, protected from light. Resorufin fluorescence was measured in a microplate reader (Biotek) using excitation at 530 nm and emission at 590 nm.

Pharmacophore Modeling and Database Searches

The details of pharmacophore model generation were provided in the main text. The initial pharmacophore modeling was carried using the Phase module in the Schrödinger software.

Additional pharmacophore modeling was carried out with Spartan 10 (V.1.1.0).

The database searches were performed flexibly, with conformations generated on-the-fly while keeping the initial conformations stored in the database. The following settings were used for searching:
1. Generate conformations during search
2. Keep existing conformers
3. Number of conformers per rotatable bond=10
4. Maximum number of conformers per structure=100
5. Sampling=Thorough
6. Amide bonds=Vary conformation
7. Relative Energy window=10.0 kcal/mol
8. Skip conformer generation for structures with >15 rotatable bonds For matching options, Intersite Distance Matching Tolerance (IDMT) was used to tighten or relax the fitting requirements. If the search retrieved more than 1000 hits, the search was set to stop. The search was then resubmitted with a smaller IDMT until a hitlist of less than 1000 was achieved. Follow-up searches were pursued with reduced IDMT until only a handful of compounds were retrieved. All searches with 1000 hits and 0 hits were removed from the Project Table. This systematic tightening of the IDMT is analogous to shrink-wrapping. The typical starting IDMT value was 2.0 Å. Hit Treatment options are left at the default values with the number of hits at 1000 used as a termination point.

The invention claimed is:
1. A compound having formula I

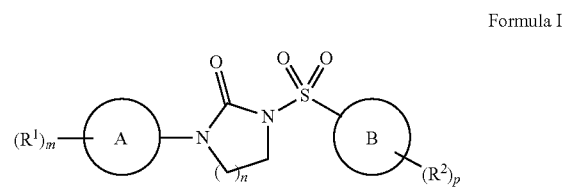

Formula I derivatives, prodrugs, esters, or salts thereof wherein,
ring A is a carbocyclyl, aryl, or heterocyclyl;
ring B is a carbocyclyl, aryl, or heterocyclyl;
n is 2;
m is 1, 2, 3, or 4;
p is 1, 2, 3, or 4;
$R^1$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{15}$;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;
$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;

$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1 having formula IA:

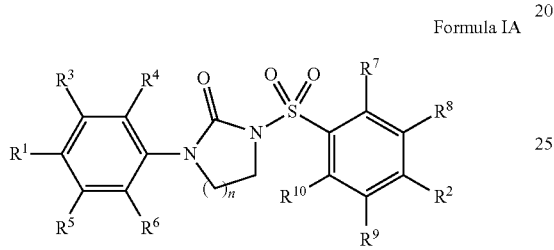

Formula IA derivatives, prodrugs, esters, or salts thereof wherein, n is 2;

$R^1$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^3$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^4$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^5$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^6$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^7$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^8$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^9$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl; and $R^{10}$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl.

3. The compound of claim 1 having formula IB:

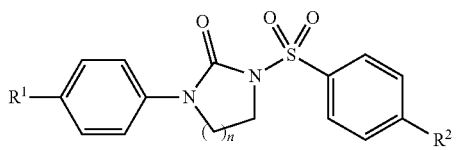

Formula IB derivatives, prodrugs, esters, or salts thereof wherein,
n is 2;
$R^1$ is alkyl optionally substituted with one or more substituents; and
$R^2$ is halogen or alkoxy optionally substituted with one or more substituents.

4. The compound of claim 3, wherein $R^1$ is alkyl substituted with one or more halogen.

5. The compound of claim 3, wherein $R^1$ is trifluoromethyl.

6. The compound of claim 3, wherein $R^2$ is halogen or alkoxy.

7. The compound of claim 3 selected from:
1-((4-methoxyphenyl)sulfonyl)-3-(4-(trifluoromethyl)phenyl)tetrahydropyrimidin-2(1H)-one; and
1-((4-fluorophenyl)sulfonyl)-3-(4-(trifluoromethyl)phenyl)tetrahydropyrimidin-2(1H)-one.

8. A pharmaceutical composition comprising a compound of claim 1 and a pharmaceutically acceptable excipient.

9. The pharmaceutical composition of claim 8 in the form of a tablet, capsule, pill, gel, or granules.

10. The pharmaceutical composition of claim 8 in the form of an aerosol, aqueous buffer or emulsion.

11. A compound having formula I

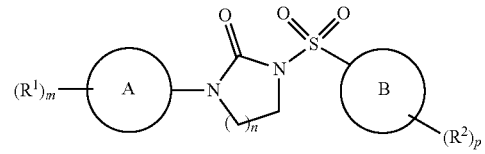

Formula I derivatives, prodrugs, esters, or salts thereof wherein,
ring A is a carbocyclyl, aryl, or heterocyclyl;
ring B is a carbocyclyl, aryl, or heterocyclyl;
n is 1;
m is 1, 2, 3, or 4;
p is 1, 2, 3, or 4;
$R^1$ is alkyl substituted with one or more halogen;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^{15}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;
$R^{16}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;
$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methyl sulfamoyl, N-ethylsulfamoyl, N,N-dim ethyl sulfamoyl, N,N-di ethyl sulfamoyl, N-methyl-N-ethylsulfamoyl, carbocyclyl, aryl, or heterocyclyl.

12. The compound of claim 11 having formula IA:

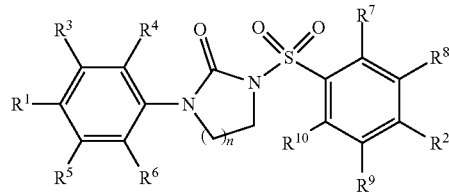

Formula IA derivatives, prodrugs, esters, or salts thereof wherein, n is 1;

$R^1$ is alkyl substituted with one or more halogen;

$R^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^3$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^4$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^5$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^6$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^7$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^8$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl;

$R^9$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl; and $R^{10}$ is hydrogen, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl.

13. The compound of claim 11 having formula IB:

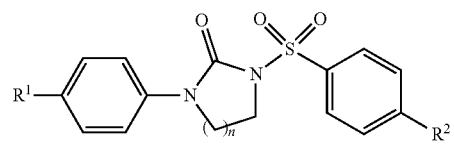

Formula IB derivatives, prodrugs, esters, or salts thereof wherein,
n is 1;
$R^1$ is alkyl substituted with one or more halogen; and
$R^2$ is halogen or alkoxy optionally substituted with one or more substituents.

14. The compound of claim 13, wherein $R^1$ is trifluoromethyl.

15. The compound of claim 13, wherein $R^2$ is halogen or alkoxy.

16. The compound of claim 13, wherein the compound is 1-((4-methoxyphenyl)sulfonyl)-3-(4-(trifluoromethyl)phenyl)imidazolidin-2-one or salts thereof.

17. A pharmaceutical composition comprising a compound of claim 11 and a pharmaceutically acceptable excipient.

18. The pharmaceutical composition of claim 11 in the form of a tablet, capsule, pill, gel, or granules.

19. The pharmaceutical composition of claim 11 in the form of an aerosol, aqueous buffer, or emulsion.

\* \* \* \* \*